(12) United States Patent
Bahrami et al.

(10) Patent No.: US 9,205,202 B2
(45) Date of Patent: *Dec. 8, 2015

(54) NEEDLE ARRAY ASSEMBLY AND METHOD FOR DELIVERING THERAPEUTIC AGENTS

(71) Applicant: Fred Hutchinson Cancer Research Center, Seattle, WA (US)

(72) Inventors: S. Bahram Bahrami, Emeryville, CA (US); Mandana Veiseh, Emeryville, CA (US); James M. Olson, S. Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/178,060

(22) Filed: Feb. 11, 2014

(65) Prior Publication Data

US 2014/0162360 A1 Jun. 12, 2014

Related U.S. Application Data

(63) Continuation of application No. 13/330,044, filed on Dec. 19, 2011, now Pat. No. 8,834,428, which is a continuation of application No. 13/048,721, filed on Mar. 15, 2011, now abandoned, which is a (Continued)

(51) Int. Cl.
*A61M 5/00* (2006.01)
*A61M 5/32* (2006.01)
(Continued)

(52) U.S. Cl.
CPC ........... *A61M 5/3298* (2013.01); *A61M 5/1452* (2013.01); *A61M 5/16827* (2013.01);
(Continued)

(58) Field of Classification Search
CPC ............ A61M 5/3298; A61M 5/3287; A61M 5/3291; A61N 1/325; A61N 1/327
USPC .................... 604/46, 154, 155, 191
See application file for complete search history.

(56) References Cited

U.S. PATENT DOCUMENTS 4,256,153 A * 3/1981 Lamaziere ...................... 141/84
4,966,159 A 10/1990 Maganias
(Continued)

FOREIGN PATENT DOCUMENTS

JP 63-315064 A 12/1988
JP H 01-122758 U 8/1989
(Continued)

OTHER PUBLICATIONS

Laske, et al. Efficacy of direct intratumoral therapy with targeted protein toxins for solid human gliomas in nude mice. J Neurosurg. Mar. 1994;80(3):520-6.
(Continued)

*Primary Examiner* — Laura Bouchelle
*Assistant Examiner* — Diva K Chander
(74) *Attorney, Agent, or Firm* — Wilson Sonsini Goodrich & Rosati

(57) ABSTRACT

A fluid delivery device includes an array of needles, each in fluid communication with a respective reservoir. Respective actuators are coupled so as to be operable to drive fluid from the reservoirs via needle ports. Each needle can have a plurality of ports, and the ports can be arranged to deliver a substantially equal amount of fluid at any given location along its length. A driver is coupled to the actuators to selectively control the rate, volume, and direction of flow of fluid through the needles. The device can simultaneously deliver a plurality of fluid agents along respective axes in solid tissue in vivo. If thereafter resected, the tissue can be sectioned for evaluation of an effect of each agent on the tissue, and based on the evaluation, candidate agents selected or deselected for clinical trials or therapy, and subjects selected or deselected for clinical trials or therapeutic treatment.

48 Claims, 9 Drawing Sheets

Related U.S. Application Data continuation of application No. 12/674,146, filed as application No. PCT/US2008/073212 on Aug. 14, 2008, now Pat. No. 8,349,554.

(60) Provisional application No. 60/955,676, filed on Aug. 14, 2007.

(51) Int. Cl.
   *A61M 5/145* (2006.01)
   *A61M 5/168* (2006.01)
   *A61M 5/20* (2006.01)
   *A61B 6/00* (2006.01)

(52) U.S. Cl.
   CPC .............. *A61M 5/20* (2013.01); *A61M 5/3287* (2013.01); *A61M 5/3291* (2013.01); *A61M 5/3294* (2013.01); *A61B 6/508* (2013.01); *A61M 5/14526* (2013.01); *A61M 2205/50* (2013.01); *A61M 2205/52* (2013.01)

(56) References Cited

U.S. PATENT DOCUMENTS

| | | | |
|---|---|---|---|
| 5,104,620 A | | 4/1992 | Wiley et al. |
| 5,154,181 A * | | 10/1992 | Fishman ................ 600/556 |
| 5,250,023 A | | 10/1993 | Lee et al. |
| 5,335,670 A | | 8/1994 | Fishman |
| 5,457,041 A | | 10/1995 | Ginaven et al. |
| 5,536,267 A * | | 7/1996 | Edwards et al. ............ 606/41 |
| 5,538,134 A | | 7/1996 | Pitesky et al. |
| 5,693,341 A | | 12/1997 | Schroeder et al. |
| 5,735,288 A | | 4/1998 | Fishman |
| 5,846,225 A * | | 12/1998 | Rosengart et al. ......... 604/115 |
| 5,876,380 A * | | 3/1999 | Manganini et al. ........ 604/191 |
| 5,993,434 A | | 11/1999 | Dev et al. |
| 6,146,594 A * | | 11/2000 | De Graaff et al. ......... 422/501 |
| 6,208,893 B1 * | | 3/2001 | Hofmann ............ A61N 1/325 604/21 |
| 6,286,455 B1 * | | 9/2001 | Williams .................... 119/6.8 |
| 6,330,479 B1 | | 12/2001 | Stauffer |
| 6,428,504 B1 | | 8/2002 | Riaziat et al. |
| 6,468,247 B1 | | 10/2002 | Zamoyski |
| 6,482,187 B1 * | | 11/2002 | Gibbs ......................... 604/218 |
| 6,558,361 B1 | | 5/2003 | Yeshurun |
| 6,685,913 B1 | | 2/2004 | Thakur |
| 6,972,013 B1 | | 12/2005 | Zhang et al. |
| 7,226,439 B2 | | 6/2007 | Prausnitz et al. |
| 7,621,895 B2 | | 11/2009 | Willis et al. |
| 7,627,938 B2 | | 12/2009 | Kim et al. |
| 7,691,085 B2 * | | 4/2010 | Dedig et al. ............... 604/151 |
| 7,711,409 B2 | | 5/2010 | Keppel et al. |
| 7,846,488 B2 * | | 12/2010 | Johnson et al. ............ 427/2.1 |
| 7,905,854 B2 | | 3/2011 | Hazut et al. |
| 7,922,672 B2 | | 4/2011 | Hein et al. |
| 7,935,086 B2 * | | 5/2011 | Lafferty, IV ............... 604/191 |
| 8,349,554 B2 | | 1/2013 | Bahrami et al. |
| 8,475,412 B2 | | 7/2013 | Bahrami et al. |
| 8,657,786 B2 | | 2/2014 | Bahrami et al. |
| 8,672,887 B2 | | 3/2014 | Bahrami et al. |
| 8,834,428 B2 | | 9/2014 | Bahrami et al. |
| 8,926,567 B2 | | 1/2015 | Bahrami et al. |
| 2002/0010439 A1 | | 1/2002 | Miller |
| 2002/0031473 A1 | | 3/2002 | Perez-Soler |
| 2002/0082546 A1 | | 6/2002 | Crank et al. |
| 2003/0060780 A1 | | 3/2003 | Shu |
| 2003/0069543 A1 | | 4/2003 | Carpenter et al. |
| 2004/0064098 A1 | | 4/2004 | Cuschieri et al. |
| 2004/0138622 A1 | | 7/2004 | Palasis |
| 2005/0187303 A1 | | 8/2005 | Wu et al. |
| 2005/0203464 A1 | | 9/2005 | Haider et al. |
| 2006/0015058 A1 | | 1/2006 | Kellogg et al. |
| 2006/0058966 A1 | | 3/2006 | Bruckner |
| 2006/0079846 A1 * | | 4/2006 | Williams ................... 604/191 |
| 2006/0259006 A1 * | | 11/2006 | McKay et al. ............. 604/506 |
| 2007/0021717 A1 | | 1/2007 | Gabel et al. |
| 2007/0142842 A1 | | 6/2007 | Krueger et al. |
| 2007/0238985 A1 | | 10/2007 | Smith et al. |
| 2007/0239099 A1 * | | 10/2007 | Goldfarb et al. ............ 604/20 |
| 2008/0009802 A1 | | 1/2008 | Lambino et al. |
| 2008/0167601 A1 | | 7/2008 | Laermer et al. |
| 2009/0149897 A1 | | 6/2009 | Dacey et al. |
| 2010/0262001 A1 * | | 10/2010 | Morris et al. ............... 600/424 |
| 2010/0291592 A1 | | 11/2010 | Semba |
| 2010/0330589 A1 | | 12/2010 | Bahrami et al. |
| 2011/0150919 A1 | | 6/2011 | Reed et al. |
| 2011/0230736 A1 * | | 9/2011 | Tepper et al. .............. 600/309 |
| 2011/0230839 A1 | | 9/2011 | Bahrami et al. |
| 2012/0087866 A1 | | 4/2012 | Bahrami et al. |
| 2012/0089095 A1 | | 4/2012 | Bahrami et al. |
| 2012/0094866 A1 | | 4/2012 | Bahrami et al. |
| 2012/0109104 A1 | | 5/2012 | Bahrami et al. |
| 2012/0121514 A1 | | 5/2012 | Bahrami et al. |
| 2012/0265064 A1 | | 10/2012 | Bahrami et al. |
| 2012/0296206 A1 | | 11/2012 | Bahrami et al. |
| 2014/0162901 A1 | | 6/2014 | Bahrami et al. |
| 2014/0309590 A1 | | 10/2014 | Bahrami et al. |

FOREIGN PATENT DOCUMENTS

| | | |
|---|---|---|
| JP | 2632367 B2 | 7/1997 |
| JP | 2000-513725 A | 10/2000 |
| JP | 2003-290343 A | 10/2003 |
| JP | 2006239260 A1 | 9/2006 |
| JP | 2007-130028 A | 5/2007 |
| JP | 2009-528131 A | 8/2009 |
| JP | 2011-506630 A | 3/2011 |
| WO | WO 94/07553 A1 | 4/1994 |
| WO | WO 97/14459 A1 | 4/1997 |
| WO | WO/00/05339 A1 | 2/2000 |
| WO | WO 00/06770 A1 | 2/2000 |
| WO | WO 00/56381 A1 | 9/2000 |
| WO | WO 00/56395 A1 | 9/2000 |
| WO | WO 00/74766 A1 | 12/2000 |
| WO | WO 00/074766 A1 | 12/2000 |
| WO | WO 03/075978 A2 | 9/2003 |
| WO | WO 2004/012791 A2 | 2/2004 |
| WO | WO 2007/016529 A2 | 2/2007 |
| WO | WO 2007/030367 A2 | 3/2007 |
| WO | WO 2007/016529 A3 | 4/2007 |
| WO | WO 2007/103070 A2 | 9/2007 |
| WO | WO 2008/008845 A2 | 1/2008 |
| WO | WO 2008/008845 A3 | 4/2008 |
| WO | WO 2007/103070 A3 | 8/2008 |
| WO | WO 2009/023798 A2 | 2/2009 |
| WO | WO 2009/023798 A3 | 5/2009 |

OTHER PUBLICATIONS

Notice of allowance dated Mar. 4, 2013 for U.S. Appl. No. 13/329,701.
Notice of allowance dated Jun. 6, 2014 for U.S. Appl. No. 13/330,044.
Notice of allowance dated Oct. 10, 2013 for U.S. Appl. No. 13/330,022.
Notice of allowance dated Nov. 11, 2013 for U.S. Appl. No. 13/330,106.
Office action dated Jul. 1, 2014 for U.S. Appl. No. 13/330,124.
Sheu, et al. Small hepatocellular carcinoma: intratumor ethanol treatment using new needle and guidance systems. Radiology. Apr. 1987;163(1):43-8.
Third party observations dated Aug. 29, 2014 against EP Application No. 08797923.3.
Weissleder, et al. In vivo imaging of tumors with protease-activated near-infrared fluorescent probes. Nat Biotechnol. Apr. 1999;17(4):375-8.
U.S. Appl. No. 14/178,022, filed Feb. 11, 2014, Bahrami et al.
U.S. Appl. No. 14/178,045, filed Feb. 11, 2014, Bahrami et al.
City of Hope. Brain Tumor Research. Available at http://www.cityofhope.org/PATIENT_CARE/TREATMENTS/BRAIN-TU-MORS/Pages/research-and-clinical-trials.aspx. Accessed May 3, 2010.

(56) References Cited

OTHER PUBLICATIONS

European Search report and search opinion dated Feb. 1, 2011 for EP application No. 08797923.3.
Inovio. Intramuscular Delivery. Available at http://www.inovio.com/technology/intramusculardelivery.htm. Accessed Mar. 19, 2010.
International search report dated Apr. 6, 2009 for PCT Application No. US2008/73212.
Lin, et al. Ablation of liver tumor by injection of hypertonic saline. AJR Am J Roentgenol. Jan. 2005;184(1):212-9.
Notice of allowance Nov. 28, 2012 for U.S. Appl. No. 12/674,146.
Office action dated Mar. 1, 2013 for U.S. Appl. No. 13/330,124.
Office action dated Mar. 4, 2013 for U.S. Appl. No. 13/330,022.
Office action dated Apr. 11, 2013 for U.S. Appl. No. 13/330,106.
Office action dated Oct. 4, 2013 for U.S. Appl. No. 13/330,044.
Office action dated Oct. 8, 2013 for U.S. Appl. No. 13/330,124.
Office action dated Oct. 12, 2012 for U.S. Appl. No. 13/048,721.
Office action dated Oct. 17, 2011 for U.S. Appl. No. 13/048,721.
Procter & Gamble. Inexpensive Micro-Needle Array for Drug Delivery, Biological Sensing. Available at http://www.yet2.com/app/insight/techofweek/30761?sid=350. Accessed Mar. 19, 2010.
Search report dated Nov. 11, 2010 for GB Application No. GB1004138.2.
Sharma, et al. Intra-tumoral injection of CpG results in the inhibition of tumor growth in murine Colon-26 and B-16 tumors. Biotechnol Lett. Jan. 2003;25(2):149-53.
Victor-g.com. Cass needle—Bent/Straight. Available at http://www.victor-g.com/irrigation_needles.htm#Cass. Accessed May 3, 2010.
Victor-g.com. Irrigation/side port needles. Available at http://www.victor-g.com/irrigation_needles.htm. Accessed May 3, 2010.
World Wide Medical Technologies. Our products: Bone marrow systems. Available at http://www.wwmedtech.com/aspircore.php. Accessed May 3, 2010.
Office action dated Mar. 27, 2014 for U.S. Appl. No. 13/330,044.
Notice of allowance dated Oct. 8, 2014 for U.S. Appl. No. 13/330,124.
Office action dated Oct. 8, 2014 for U.S. Appl. No. 14/178,045.
Office action dated Jul. 2, 2015 for U.S. Appl. No. 13/489,594.
Notice of allowance dated Sep. 8, 2015 for U.S. Appl. No. 14/178,045.

\* cited by examiner

NEEDLE ARRAY ASSEMBLY AND METHOD FOR DELIVERING THERAPEUTIC AGENTS

CROSS-REFERENCE TO RELATED APPLICATIONS

This application is a continuation of U.S. application Ser. No. 13/330,044 filed Dec. 19, 2011, which is a continuation of U.S. application Ser. No. 13/048,721, filed Mar. 15, 2011, which is a continuation of U.S. application Ser. No. 12/674,146, filed Aug. 27, 2010, which is a national stage application of PCT/US2008/73212, filed Aug. 14, 2008, which claims the benefit under 35 U.S.C. §119(e) of U.S. Provisional Patent Application No. 60/955,676 filed Aug. 14, 2007. The contents of each of the above-named documents are incorporated herein by reference for all purposes in their entirety.

STATEMENT REGARDING FEDERALLY SPONSORED RESEARCH OR DEVELOPMENT

This invention was made with support of the United States government under grant number 5R42CA144104-03 awarded by the National Institutes of Health. The government has certain rights in the invention.

BACKGROUND

1. Technical Field

In general, the disclosed embodiments relate to devices and methods for the introduction and subsequent evaluation of therapeutic agents to biological tissue, and in particular to the simultaneous introduction of a plurality of agents to the tissue in vivo.

2. Description of the Related Art

Numerous cancer-related therapeutics are under phase I or phase II clinical trial and evaluations at any particular time; however, most of them will fail to advance. In fact, it is estimated that more than 90% of cancer-related therapeutics will fail phase I or II clinical trial evaluation. The failure rate in phase III trials is almost 50%, and the cost of new drug development from discovery through phase III trials is between $0.8 billion and $1.7 billion and can take between eight and ten years.

In addition, many patients fail to respond even to standard drugs that have been shown to be efficacious. For reasons that are not currently well understood or easily evaluated, individual patients may not respond to standard drug therapy. One significant challenge in the field of oncology is to exclude drug selection for individual patients having cell autonomous resistance to a candidate drug to reduce the risk of unnecessary side effects. A related problem is that excessive systemic concentrations are required for many oncology drug candidates in efforts to achieve a desired concentration at a tumor site, an issue compounded by poor drug penetration in many under-vascularized tumors (Tunggal et al., 1999 *Clin. Canc. Res.* 5:1583).

Clearly there is a need in the art for improved devices and methods for testing and delivering cancer therapies, including improved methodologies for performing efficient pre-clinical and clinical studies of candidate oncology medicines, and for identifying therapeutics having increased likelihood of benefiting individual subjects. The present invention addresses these and similar needs, and offers other related advantages.

BRIEF SUMMARY

It is an aspect of the present invention to provide a device for delivery of a fluid to a solid tissue, comprising: a plurality of needles arranged in an array; a plurality of reservoirs, each in fluid communication with a respective one of the plurality of needles; and a plurality of actuators operatively coupled to respective ones of the plurality of reservoirs and configured to control a fluid pressure within the reservoir. In certain embodiments each of the plurality of actuators comprises one of a plurality of plungers, a first end of each of the plurality of plungers being received in a respective one of the plurality of reservoirs, and in certain further embodiments the plungers of the plurality of plungers are operatively coupled together at respective second ends so as to be simultaneously depressable. Certain still further embodiments comprise a plunger driver configured to depress all of the plurality of plungers at a selectively variable rate. In other embodiments each of the plurality of actuators comprises one of a plurality of fluid transmission lines having first and second ends, a first end of each of the plurality of fluid transmission lines being coupled to a respective one of the plurality of reservoirs. In other embodiments the device comprises a fluid pressure source, and each of the plurality of actuators comprises a fluid coupling between the fluid pressure source and a respective one of the plurality of reservoirs. In further embodiments the fluid pressure source comprises at least one of a compressor, a vacuum accumulator, a peristaltic pump, a master cylinder, a microfluidic pump, and a valve. In another embodiment, each of the plurality of needles comprises a plurality of ports distributed along its length.

In another embodiment there is provided a device for delivering a fluid to a solid tissue, comprising a dispenser including a needle having a plurality of ports distributed along a length thereof, a reservoir in fluid communication with the dispensing needle, and a plunger having a first end positioned in the reservoir; and a plunger driver coupled to a second end of the plunger and configured to depress the plunger at a selectably variable rate. In certain further embodiments the dispenser is one of a plurality of dispensers arranged in a dispenser array, each comprising a needle, a reservoir, and a plunger having first and second ends. In certain further embodiments the plunger driver is coupled to the second end of the plunger of each of the plurality of dispensers and is configured to depress each of the plungers simultaneously. In certain other further embodiments the device comprises a plurality of cylindrical tubes arranged in an array corresponding to the dispenser array, each of the plurality of cylindrical tubes being sized and positioned to receive the needle of a respective one of the plurality of dispensers.

In certain other embodiments the plunger driver comprises a driver shaft coupled to the plunger and having a threaded region, the plunger driver configured such that rotation of the driver shaft in a first direction depresses the plunger a distance corresponding to a thread pitch of the threaded region and a number of revolutions of the driver shaft. In certain further embodiments the device comprises a motor having a rotor coupled to the driver shaft of the plunger driver such that the rotor and the driver shaft are rotationally fixed with respect to each other, the motor being controllable to rotate the rotor at a selectably variable rate. In certain other further embodiments the device comprises a motor having a rotor coupled to the driver shaft of the plunger driver such that the rotor and the driver shaft are rotationally fixed with respect to each other, the motor being controllable to rotate the rotor to a selectable angle of rotation. Certain further embodiments comprise a controller coupled to the motor, the controller being programmable to control direction and speed of rotation of the rotor and to control a number of degrees from a start of rotation to an end of rotation. In other embodiments of the above described device, the dispenser comprises a dispenser cylinder; a first portion of the dispenser cylinder defines the reservoir; and a second portion of the dispenser cylinder defines the needle. In another embodiment the plurality of ports are sized and positioned along the length of the needle so as to deliver a substantially equal amount of fluid at any given location along the length of the needle. In another embodiment the plurality of ports is evenly distributed along a portion of the length of the needle.

In certain embodiments a size of each of the plurality of ports is inversely related to a distance of the respective port from a tip-end of the needle. In certain other embodiments a distribution density of the plurality of ports is inversely related to a distance of the respective port from a tip-end of the needle. In certain other embodiments the plurality of ports is distributed in a spiral pattern along the length of the needle. In certain other embodiments the plurality of ports is arranged in pairs of ports on opposite sides of the needle, with each pair of ports rotated 90 degrees with respect to adjacent pairs of ports along the length of the needle.

According to certain other embodiments disclosed herein, there is provided a method, comprising placing an agent in a reservoir of each of a plurality of dispenser needles; inserting each of the plurality of dispenser needles into a selected region of solid tissue; and introducing the agent in the reservoirs into the selected region of solid tissue by simultaneously overpressurizing each of the plurality of dispenser needles. In certain further embodiments the introducing comprises introducing the agent in the reservoirs into the selected region of solid tissue from a plurality of apertures along each of the plurality of dispenser needles. Certain other further embodiments comprise at least one of imaging the solid tissue prior to the inserting, imaging the solid tissue concurrently with the inserting, and imaging the solid tissue after the inserting. In certain other further embodiments the inserting comprises inserting an array of introducer needles into a subject; inserting each of the plurality of dispenser needles into a respective one of the array of introducer needles; and extending a tip-end of each of the plurality of dispenser needles beyond a tip end of the respective one of the array of introducer needles and into the selected region of tissue. Certain further embodiments comprise removing stylets from the introducer needles of the array prior to inserting the plurality of dispenser needles.

In certain embodiments the selected region of tissue is a portion of a tumor in a subject, and in certain further embodiments the subject is one of a preclinical model and a human patient. In certain other embodiments the method comprises excising at least the portion of the tumor after the introducing. Certain further embodiments comprise at least one of imaging the tumor prior to the excising, imaging the tumor concurrently with the excising, and imaging the tumor after to the excising. In certain other embodiments the excising comprises excising at least the portion of the tumor at a time that is a selected period of time after introducing the agent. In certain further embodiments the selected period of time is one of a range of time, a minimum period of time for excising, and a specific period of time for excising. In certain embodiments the selected period of time is a period exceeding 48 hours. In certain embodiments the selected period of time is a range of between about 72 and about 96 hours. In certain embodiments the selected period of time is a period exceeding one week.

According to certain other embodiments of the above described method, the agent comprises a plurality of agents, and the placing comprises placing each of the plurality of agents into the reservoir of a respective one of the plurality of dispenser needles. In certain further embodiments the plurality of agents comprises at least one of a negative control composition and a positive control composition. In certain other further embodiments the plurality of agents comprises at least one position marker. In certain other further embodiments at least one of the plurality of agents is a candidate effective agent. In certain other further embodiments at least one of the plurality of agents comprises an indicator of efficacy, which in certain further embodiments comprises at least one of a nanoparticle, a nanostructure, and an indicator dye. In certain other embodiments at least one of the plurality of agents is selected based on a clinically demonstrated efficacy of the respective agent. In certain other further embodiments of the above described method, the method comprises assessing, with respect to at least one of the plurality of agents, at least one of efficacy, activity, and toxicity of the agent.

In another embodiment there is provided a method for identifying relative efficacies of a plurality of agents for treating a subject, comprising injecting each of a plurality of candidate effective agents into a respective location in an injection site in a solid tissue in a subject; excising from the subject at least the injection site of the solid tissue; and evaluating the excised injection site for an altered physiologic state at each of the respective locations, and therefrom identifying relative efficacies of the plurality of agents. In certain further embodiments the excising comprises one of excising at least 48 hours after the injecting, excising at least 72 hours after the injecting, excising 72 to 96 hours after the injecting, and excising at least one week after the injecting.

In another embodiment there is provided a method of operation of a therapeutic device, comprising charging a reservoir of each of a plurality of needles with a respective one of a plurality of agents; injecting, simultaneously, each of the plurality of agents into a respective region of a solid tissue; and evaluating an effect of each of the plurality of agents on the respective region. In certain further embodiments the injecting comprises injecting the plurality of agents into the solid tissue in vivo, and in certain still further embodiments the method comprises excising the solid tissue prior to the evaluating. In certain embodiments the method comprises imaging the solid tissue, which in certain further embodiments comprises imaging the solid tissue in vivo. In certain other embodiments the injecting comprises distributing each of the plurality of agents into the solid tissue along an axis in the respective region of the tissue. In certain other embodiments the method further comprises assessing, with respect to at least one of the plurality of agents, at least one of efficacy, activity, and toxicity of the agent.

Also provided herein according to certain embodiments is a method of determining efficacy of a cancer treatment regimen, comprising simultaneously introducing an agent to a plurality of positions in a solid tumor in a subject in vivo; removing the tumor from the subject; and evaluating an effect of the agent on the tumor in vitro. In certain further embodiments the agent comprises a plurality of agents and the introducing comprises distributing each of the plurality of agents to a respective one of the plurality of positions in the tumor. In another embodiment there is provided a method, comprising introducing an agent to a region of solid tissue in a subject by distributing the agent to a plurality of positions along an axis within the region of solid tissue in vivo; removing the region of solid tissue from the subject; and evaluating an effect of the agent on the region of solid tissue in vitro. In a further embodiment the region of solid tissue comprises a tumor.

In certain embodiments the axis is one of a plurality of parallel axes in the region of solid tissue, and wherein the introducing comprises distributing the agent along each of the plurality of parallel axes. In certain further embodiments the introducing comprises simultaneously distributing the agent along each of the plurality of parallel axes, and in certain other further embodiments the plurality of parallel axes is arranged in an array. In certain other embodiments the method comprises introducing at least two position markers to the region of solid tissue along a respective one of the plurality of parallel axes, and in certain further embodiments the introducing at least two position markers comprises distributing the at least two position markers along respective parallel axes within the region of solid tissue. In certain other embodiments the at least two position markers each comprise a detectable label that is selected from the group consisting of a radiolabel, a radio-opaque label, a fluorescent label, a colorimetric label, a dye, an enzymatic label, a GCMS tag, avidin, and biotin.

In certain other embodiments of the above described method, the agent is one of a plurality of agents and the axis is one of a plurality of parallel axes arranged in an array in the region of solid tissue, and wherein the introducing comprises distributing each of the plurality of agents to a plurality of positions along a respective one of the plurality of parallel axes. In certain other embodiment the method comprises at least one of imaging the solid tissue prior to the introducing, imaging the solid tissue concurrently with the introducing, and imaging the solid tissue after the introducing. In certain other embodiments the evaluating comprises sectioning the region of solid tissue into a plurality of sections normal to the parallel axes. In certain further embodiments the evaluating comprises detecting within the solid tissue an altered physiologic state that results from at least one of the plurality of agents. In certain further embodiments the detecting comprises, with respect to the at least one of the plurality of agents, at least one of detecting a degree of permeation of the agent through the solid tissue, detecting a physicochemical effect of the agent on the tissue, and detecting a pharmacological effect of the agent on the tissue. In certain other embodiments the evaluating comprises determining the effects of at least two of the plurality of agents on a same position within the region of the solid tissue. In certain other embodiments the evaluating comprises determining the effects of at least two of the plurality of agents on adjacent positions within the region of the solid tissue.

In certain other embodiments the evaluating comprises differentiating a degree of the effect of at least one of the plurality of agents on different sections of the solid tissue according to different characteristics of the different sections of the solid tissue. In certain other embodiments the evaluating comprises comparing a first effect of at least a first one of the plurality of agents on the solid tissue with a second effect of at least a second one of the plurality of agents on the solid tissue. In certain other embodiments the evaluating comprises, with respect to at least one of the plurality of agents, assessing at least one of efficacy, activity, and toxicity on the region of solid tissue. In certain other embodiments the method comprises deselecting at least one of the plurality of agents based on the evaluating. In certain other embodiments the method comprises selecting at least one of the plurality of agents based on the evaluating. In certain other embodiments the method comprises prioritizing at least two of the plurality of agents based on the evaluating. In certain other embodiments the method comprises distributing the plurality of agents to a plurality of positions, each along a respective one of a plurality of parallel axes within a region of solid tissue within each of a plurality of subjects. In certain further embodiments the method comprises one of (i) selecting at least one of the plurality of agents based on the evaluating, (ii) deselecting at least one of the plurality of agents based on the evaluating, and (iii) prioritizing at least two of the plurality of agents based on the evaluating. In certain other embodiments the method comprises one of (i) selecting at least one of the plurality of subjects based on the evaluating, (ii) deselecting at least one of the plurality of subjects based on the evaluating, and (iii) prioritizing at least two of the plurality of subjects based on the evaluating. In certain other embodiments the evaluating comprises determining a level of altered physiologic state of the solid tissue near at least one of the plurality of parallel axes.

Turning to another embodiment there is provided a fluid agent-delivering device comprising (i) a plurality of needles arranged in an array, each of said needles having, independently, one or a plurality of ports distributed along its length wherein at least one needle has said plurality of ports, (ii) a plurality of reservoirs containing the fluid agent, each of said reservoirs being in fluid communication with a respective one of the plurality of needles, and (iii) a plurality of plungers, a first end of each plunger being received in a respective one of the plurality of reservoirs and a second end of each plunger being depressable such that depressing each plunger results in injection of the fluid agent through the respective one of the plurality of needles.

In another embodiment of the presently disclosed invention there is provided a method for selective delivery of a fluid agent to a solid tissue, comprising (a) introducing a plurality of needles of a fluid agent-delivering device into the solid tissue; and (b) administering the fluid agent into the solid tissue by injection through said needles. In certain further embodiments the solid tissue has been removed from a subject. In certain other further embodiments the solid tissue is in a subject. In certain further embodiments the agent is delivered to the solid tissue in a therapeutically effective amount. In certain still further embodiments, outside the solid tissue, the agent is either (i) undetectable, or (ii) if detectable outside the solid tissue, the agent is present at less than a minimal dose. In certain embodiments the solid tissue comprises a tumor. In certain further embodiments the tumor is selected from a benign tumor and a malignant tumor. In certain other further embodiments the tumor is selected from a primary tumor, an invasive tumor and a metastatic tumor. In certain other further embodiments the tumor comprises at least one cancer cell selected from a prostate cancer cell, a breast cancer cell, a colon cancer cell, a lung cancer cell, a brain cancer cell, and an ovarian cancer cell. In certain other further embodiments the tumor comprises a cancer selected from adenoma, adenocarcinoma, squamous cell carcinoma, basal cell carcinoma, small cell carcinoma, large cell undifferentiated carcinoma, chondrosarcoma and fibrosarcoma. In certain other embodiments the solid tissue is selected from brain, liver, lung, kidney, prostate, ovary, spleen, lymph node, thyroid, pancreas, heart, skeletal muscle, intestine, larynx, esophagus and stomach.

In certain other embodiments the fluid agent comprises an agent that is selected from (a) a gene therapy agent; (b) a chemotherapy agent; (c) a small molecule; (d) an antibody; (e) a protein; (f) one of a small interfering RNA and an encoding polynucleotide therefor; (g) one of an antisense RNA and an encoding polynucleotide therefor; (h) one of a ribozyme and an encoding polynucleotide therefor; (i) a detectable label; and (j) one of a therapeutic protein, polypeptide, and a peptidomimetic. In certain further embodiments the detectable label is selected from a radiolabel, a radio-opaque label, a fluorescent label, a colorimetric label, a dye, an enzymatic label, a GCMS tag, avidin, and biotin. In certain embodiments the agent is selected from (i) a gene therapy agent that comprises at least one operably linked promoter, (ii) a small interfering RNA-encoding polynucleotide that comprises at least one operably linked promoter; (iii) an antisense RNA-encoding polynucleotide that comprises at least one operably linked promoter; and (iv) a ribozyme-encoding polynucleotide that comprises at least one operably linked promoter. In certain further embodiments the operably linked promoter is selected from a constitutive promoter and a regulatable promoter. In certain still further embodiments the regulatable promoter is selected from an inducible promoter, a tightly regulated promoter and a tissue-specific promoter.

In certain other embodiments there is provided a method for altering a physiologic state in a solid tissue, comprising: (a) introducing a plurality of needles of a fluid agent-delivering device into the solid tissue; and (b) administering the fluid agent into the solid tissue by injection through said needles.

In certain embodiments there is provided a method for obtaining biological samples from a plurality of positions in a solid tissue, comprising (a) introducing a multiple needle device into the solid tissue, thereby placing a plurality of needles at a plurality of positions in the tissue; and (b) generating negative pressure at a port of each needle of said multiple needle device under conditions and for a time sufficient to draw into said needles a plurality of biological samples from said plurality of positions in the tissue, and thereby obtaining biological samples from a plurality of positions in the tissue.

In certain embodiments there is provided a method for obtaining biological samples from a plurality of positions along an axis in a solid tissue, comprising (a) introducing a multiple needle device into the solid tissue, thereby placing a plurality of needles at a plurality of positions in the tissue; and (b) generating negative pressure at a plurality of ports located along a length of each needle of said multiple needle device under conditions and for a time sufficient to draw into said needles a plurality of biological samples from said plurality of positions in the tissue, and thereby obtaining biological samples from a plurality of positions along an axis in the tissue.

In certain embodiments there is provided a method of screening subjects for eligibility to participate in a clinical trial of one or more agents, comprising (a) introducing one or more agents to a region of solid tissue in one or more subjects in vivo by distributing each of said agents to a plurality of positions along an axis within the region in each subject; (b) removing the region of solid tissue from each of said subjects; and (c) evaluating each region removed in (b) for an effect of each agent on the respective position along the axis within the region, wherein either (i) for any given agent or agents presence of a detectable effect of said agent or agents on the solid tissue region from the subject indicates eligibility of the subject for participation in a clinical trial of the agent or agents, (ii) for any given agent or agents absence of a detectable effect of said agent or agents on the solid tissue region from the subject indicates ineligibility of the subject for participation in a clinical trial of the agent or agents, or (iii) both (i) and (ii).

In certain embodiments there is provided a method of rating a candidate agent for development into a therapeutic agent for treating a solid tumor, comprising (a) introducing one or more candidate agents to a region of a solid tumor of known tumor type in each one or more subjects having a tumor of the known tumor type, by distributing each of said candidate agents to a plurality of positions along an axis within the region in each subject; (b) removing the region of solid tumor from each of said subjects; and (c) comparing each region removed in (b) for an effect of each candidate agent on the respective position along the axis within the region, wherein an agent that results in a greater beneficial effect when introduced to the tumor receives a higher rating for development into a therapeutic agent for treating the solid tumor, and an agent that results in a lesser beneficial effect when introduced to the tumor receives a lower rating for development into a therapeutic agent for treating the solid tumor.

These and other aspects of the present invention will become apparent upon reference to the following detailed description and attached drawings.

DETAILED DESCRIPTION

Figure 1:
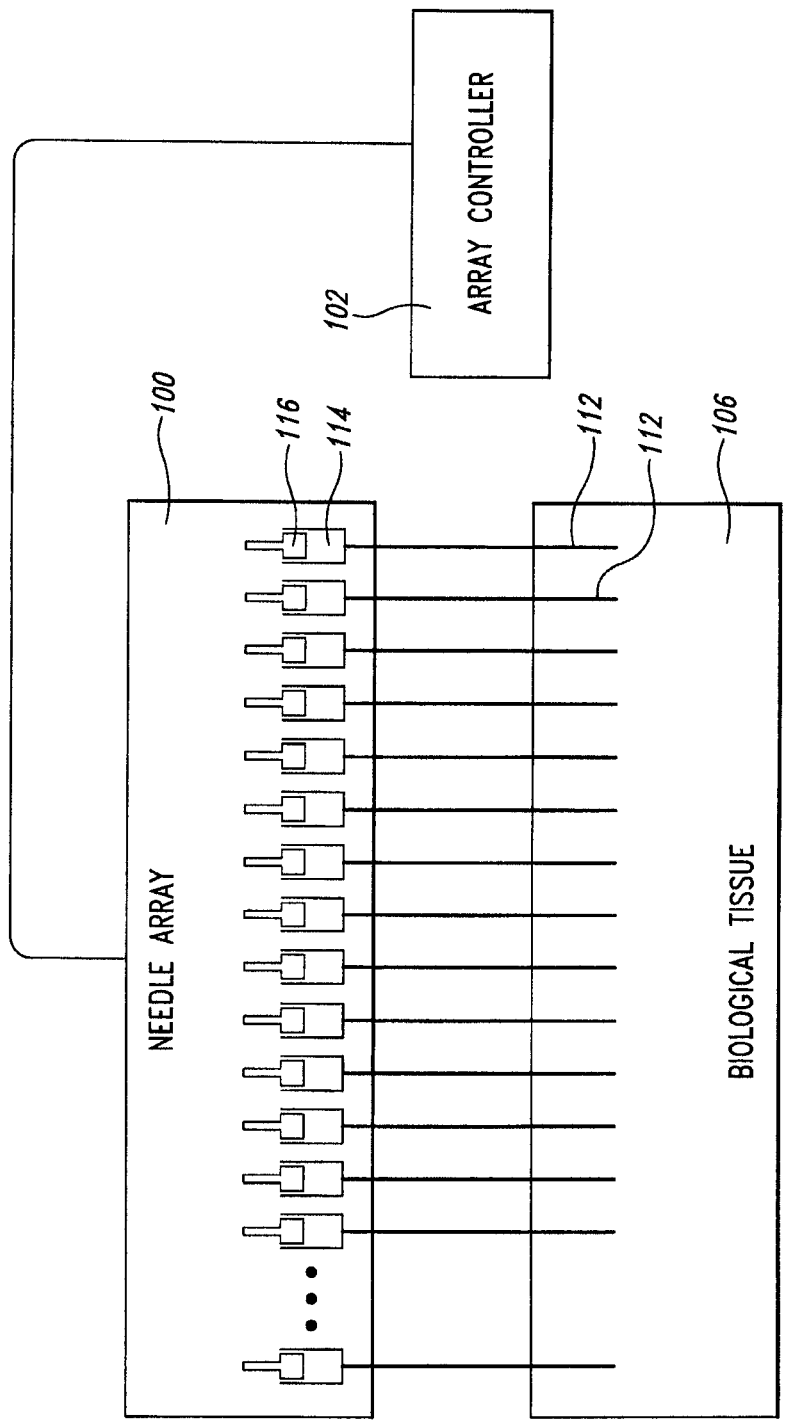
FIG. 1 is a schematic diagram of a needle array assembly for injecting biological tissue with therapeutic agents according to various embodiments.

The present invention is directed in certain embodiments as described herein to devices and methods for delivery of fluids to solid tissues, and in particular embodiments, to solid tumors. The herein described embodiments relate in part to certain surprising and heretofore unrecognized advantages, disclosed in greater detail below, that derive from exquisite control of the location, amount and time of fluid delivery to solid tissue. These and related embodiments feature the precise positioning of delivery needle outlet apertures, including positioning of spatially defined multiple-needle arrays and/or of needles having multiple outlet apertures at defined locations, and further including the use of fluidics configurations that provide extremely fine control over fluid delivery events. The invention provides improved accuracy and versatility to screening therapeutic compounds such as anti-cancer agents for use in treating solid tumors, and permits early exclusion from a screening program or a therapeutic regimen of candidate drugs to which tumor cells may be resistant.

Accordingly, for example, certain embodiments contemplate direct drug delivery to a solid tissue at low flow rates with low shear forces that eliminate or reduce mechanochemical damage to tissues while permitting precisely targeted therapeutic agent delivery to defined focal sites. These and related embodiments permit advantageous and selective delivery of a therapeutic agent to a solid tissue in vivo in a therapeutically effective amount, while in further related embodiments the agent is undetectable outside the solid tissue or is present at less than a minimal dose. Hence, problems (e.g., toxicity, detrimental side-effects, etc.) associated with administering excessively high systemic concentrations in order to obtain a therapeutically effective concentration in a desired solid tissue are overcome by the presently disclosed embodiments.

Additionally, certain embodiments contemplate direct delivery of multiple drugs, candidate drugs, imaging agents, positional markers, indicators of efficacy and appropriate control compositions to a plurality of spatially defined locations along parallel axes in a solid tissue, such as a solid tumor, followed, after a desired time interval, by excision of the treated tissue and evaluation or analysis of the tissue for effects of the treatments. Indicators of efficacy may be, for example, detectable indicator compounds, nanoparticles, nanostructures or other compositions that comprise a reporter molecule which provides a detectable signal indicating the physiological status of a cell, such as a vital dye (e.g., Trypan blue), a colorimetric pH indicator, a fluorescent compound that may exhibit distinct fluorescence as a function of any of a number of cellular physiological parameters (e.g., pH, intracellular $Ca^{2+}$ or other physiologically relevant ion concentration, mitochondrial membrane potential, plasma membrane potential, etc., see Haugland, *The Handbook: A Guide to Fluorescent Probes and Labeling Technologies* ($10^{th}$ Ed.) 2005, Invitrogen Corp., Carlsbad, Calif.), an enzyme substrate, a specific oligonucleotide probe, a reporter gene, or the like. Control compositions may be, for example, negative controls that have been previously demonstrated to cause no statistically significant alteration of physiological state, such as sham injection, saline, DMSO or other vehicle or buffer control, inactive enantiomers, scrambled peptides or nucleotides, etc.; and positive controls that have been previously demonstrated to cause a statistically significant alteration of physiological state, such as an FDA-approved therapeutic compound.

Typically and in certain preferred embodiments, the excised tissue may be cut into a plurality of serial histological sections along parallel planes that are substantially normal (e.g., perpendicular or deviating from perpendicular by as much as 1, 2, 3, 4, 5, 6, 7, 8, 9, 10, 11, 12, 13, 14, 15, 20, 25, 30, 35 or more degrees) to the parallel axes, for analysis by any of a number of known histological, histochemical, immunohistological, histopathologic, microscopic (including morphometric analysis and/or three-dimensional reconstruction), cytological, biochemical, pharmacological, molecular biological, immunochemical, imaging or other analytical techniques, which techniques are known to persons skilled in the relevant art. See, e.g., Bancroft and Gamble, *Theory and Practice of Histological Techniques* ($6^{th}$ Ed.), 2007 Churchill Livingstone, Oxford, UK; Kiernan, *Histological and Histochemical Methods Theory and Practice*, 2001 Cold Spring Harbor Laboratory Press, Cold Spring Harbor, N.Y.; M. A. Hayat (Ed.), Cancer Imaging—Vols. 1 and 2, 2007 Academic Press, NY. Imaging may be performed before, during or after dispenser needles are inserted into the solid tissue. Positional markers are known and include, as non-limiting examples, metal or plastic clips, fluorescent quantum dots, India ink, metal or plastic beads, dyes, stains, tumor paint (Veiseh et al., 2007 *Canc. Res.* 67:6882) or other positional markers, and may be introduced at desired positions. Markers may include any subsequently locatable source of a detectable signal, which may be a visible, optical, colorimetric, dye, enzymatic, GCMS tag, avidin, biotin, radiological (including radioactive radiolabel and radio-opaque), fluorescent or other detectable signal.

A detectable marker thus may comprises a unique and readily identifiable gas chromatography/mass spectrometry (GCMS) tag molecule. Numerous such GCMS tag molecules are known to the art and may be selected for use alone or in combination as detectable identifier moieties. By way of illustration and not limitation, various different combinations of one, two or more such GCMS tags may be added to individual reservoirs of the device described herein in a manner that permits the contents of each reservoir to be identified on the basis of a unique GCMS "signature", thereby permitting any sample that is subsequently recovered from an injection region to be traced back to its needle of origin for identification purposes. Examples of GCMS tags include $\alpha,\alpha,\alpha$-trifluorotoluene, $\alpha$-methylstyrene, o-anisidine, any of a number of distinct cocaine analogues or other GCMS tag compounds having readily identifiable GCMS signatures under defined conditions, for instance, as are available from SPEX CertiPrep Inc. (Metuchen, N.J.) or from SigmaAldrich (St. Louis, Mo.), including Supelco® products described in the Supelco® 2005 gas chromatography catalog and available from SigmaAldrich.

Through the use of the device described herein, which includes configuration (e.g., by placing at least one positional marker in one or more known locations) of the multiple needles in a manner that permits ready identification of the effects at a particular location, if any, of the contents released from a particular needle at the tissue location these and related embodiments thus contemplate methods of simultaneously comparing the relative therapeutic efficacies and/or toxicities of a large number of candidate therapeutic agents. Such applications may find uses in methods of drug screening and drug discovery, such as in preclinical animal models to identify and functionally characterize potential new therapeutics. For instance, a plurality of siRNAs may be administered intratumorally and their relative abilities to knock down expression of a desired target gene may be compared. Other similar embodiments may find uses in clinical contexts, for example, to "deselect", or eliminate from consideration, known therapeutic agents that have no effect in a particular tumor, thereby advantageously advancing the therapeutic management of a patient by avoiding the loss of time and the undesirable side-effects that may be associated with administering an ineffectual treatment regimen.

The present invention provides compositions and methods that are useful for the classification and/or stratification of a subject or patient population, including for use in drug discovery and in pharmacogenomics. In these and related embodiments, correlation of one or more indicia of an altered physiological state with a position at which a given candidate agent has been introduced in a solid tumor may be used to gauge the subject's responsiveness to, or the potential efficacy of, a particular therapeutic treatment; related embodiments contemplate this approach for "deselection", or elimination from consideration as potential therapies, of candidate agents in which no evidence of an altered physiological state is detected at a site of introducing in the tumor.

As described herein, determination of levels of at least one indicator of altered physiologic state may also be used to stratify a patient population for eligibility to participate in a clinical trial. These and related embodiments are contemplated as usefully providing advantages associated with evaluation of candidate therapeutic compounds at an earlier stage of development than is currently the case. For instance, it is not currently standard clinical trial practice to establish biomarker parameters (which may be the basis for exclusion of subjects) prior to Phase III studies, whereas the embodiments described herein may provide useful results even in the absence of established biomarker criteria, for example, at Phase II. Accordingly it is envisioned that through the practice of certain presently disclosed embodiments, relevant information on the properties of a candidate agent may be obtained earlier in a solid tumor oncology drug development program than has previously been the case, including in a manner which may time-efficiently and cost-effectively permit elimination from a clinical trial of subjects for whom no response or benefit can be expected based on a nonresponder result for a particular candidate agent.

For example, stratification of a patient population according to levels of at least one indicator of altered physiologic state, determined as described herein, may provide a useful marker with which to correlate the efficacy of any candidate therapeutic agent being used in cancer subjects, and/or to classify subjects as responders, nonresponders or possible responders.

Referring first to FIG. 1, a needle array assembly 100 is shown, including a plurality of needles 112, a plurality of reservoirs 114, a plurality of delivery actuators such as, in the present example, plungers 116, and a controller 102. Each of the plurality of needles 112 is fixed in position relative to the others of the plurality of needles, and the plungers are likewise operatively coupled so as to be fixed in position and simultaneously actuable. Each of the plurality of needles 112 is in fluid communication with a respective one of the plurality of reservoirs 114, and each of the plurality of plungers includes a first end positioned in a respective one of the plurality of reservoirs 114. The controller 102 is operatively coupled to second ends of each of the plurality of plungers 116. The controller is configured to control actuation of the plungers within the reservoir with respect to speed, distance, and direction of movement.

Movement of the plurality of plungers 116 in a first direction creates a negative pressure in the respective reservoirs 114, drawing a therapeutic agent or other fluid into the reservoirs via the respective needle 112, thereby charging the reservoirs. Each reservoir 114 can be charged with a different agent, or some or all of the reservoirs can be charged with a common agent. Movement of the plurality of plungers 116 in a second direction creates a positive pressure, or overpressure, in the respective reservoirs 114, forcing the contents of the reservoirs out via the respective needles 112.

In this configuration, a relatively small amount of a plurality of therapeutic agents can be simultaneously delivered directly to a region of solid tissue 106 for evaluation and analysis. In some embodiments, the amount of a therapeutic agent delivered to the tissue is less than 1 μL per needle. The evaluation of the tissue 106 and the efficacy of the different therapeutic agents delivered thereto can be used, for example, to screen potential therapeutic agents for subsequent clinical trials or to make patient-specific treatment decisions based on the relative efficacy of the therapeutic agents in the tissue 106.

According to various embodiments, any number of needles can be used. For example, as few as one, two, or three needles can be used, and according to some embodiments, more than one thousand needles can be used. According to an embodiment, each of the needles includes a plurality of ports or apertures arranged along the length of the needle.

Figure 2A:
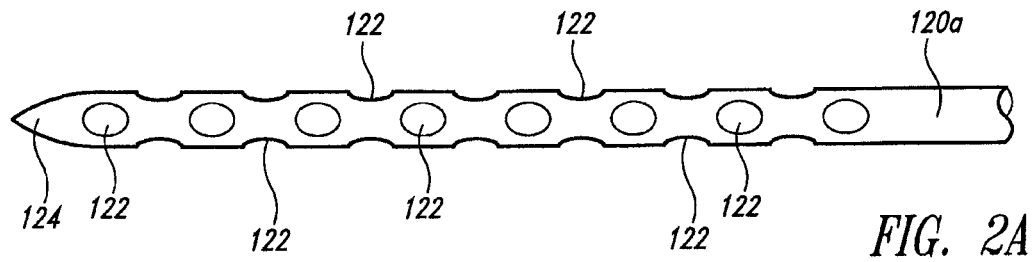
FIGS. 2A-2D and 3 show delivery needles according to respective embodiments.

Turning now to FIGS. 2A-2D, various configurations of needles 120 are shown. FIG. 2A shows a delivery needle 120a including a plurality of ports 122 in pairs on opposite sides of the needle, the pairs being evenly spaced along its length. Each pair is rotated 90 degrees with respect to adjacent pairs of ports along the length of the needle 120a. When fluid in a reservoir in fluid communication with the needle 120a is subjected to an overpressure, it is forced from the needle via the plurality of apertures 122. Because the reservoir holding the fluid is to the right of the needle 120a, as viewed in the figures, an overpressure in the reservoir will result in the largest volume of fluid being forced from the right-most ports 122, such that the fluid will be delivered in a progressively diminishing volume along its length toward the tip-end 124. The relative volume of fluid distributed from each of the plurality of ports 122 along the needle 120a may be influenced by a number of factors including, for example, viscosity of the fluid, the size and concentration of solids suspended therein, the density, permeability, and wettability of tissue in which the needle is positioned, the degree of overpressure, the size of the ports, etc.

Figure 2B:
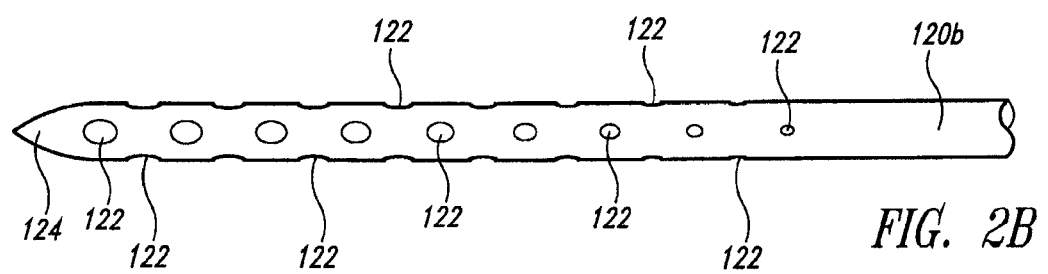

FIG. 2B shows a delivery needle 120b according to another embodiment, in which ports 122 are largest near the tip-end 124 of the needle 120b, and the relative size of each of the plurality of ports is inversely related to a distance of the respective port from the tip-end of the needle. Thus, while an overpressure of fluid in the needle will be greatest at the right-most port 122, that will also be the smallest port, and, conversely, while the overpressure will be lowest at the left-most port 122, that port will also be the largest. By appropriate sizing of each of the ports 122, the needle 120b can be configured to deliver a substantially equal volume of fluid at any given location along its axis, or alternatively, the needle can be configured to deliver fluid according to any selected distribution profile along its axis, by appropriate selection of the size of the respective ports 122. The size of the apertures can vary along the length of the needle from about 0.01 mm or less to about 0.25 mm or more.

Figure 2C:
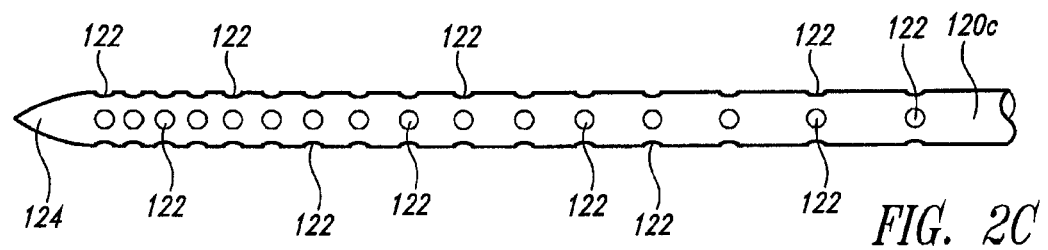

FIG. 2C shows a delivery needle 120c according to an embodiment in which a distribution density of the plurality of ports 122 is inversely related to a distance of the respective port from the tip-end 124 of the needle 120c. In other words, the ports 122 closest to the tip-end 124 of the needle 120c are the most closely spaced, while the spacing between the ports grows increasingly greater as the distance from the tip-end increases. Accordingly, when fluid in the associated reservoir is subjected to an overpressure, the volume of fluid per port 122 will be greatest at the right-most port, but a lower volume of fluid per port will be offset toward the left by the progressively closer spacing of the ports. Thus, the overall distribution of fluid along the length of the needle 120c can be made to be substantially consistent by distributing the ports 122 as described above, or can be made to conform to another selected distribution profile by appropriate selection of the distribution density of the ports along the needle.

Figure 2D:
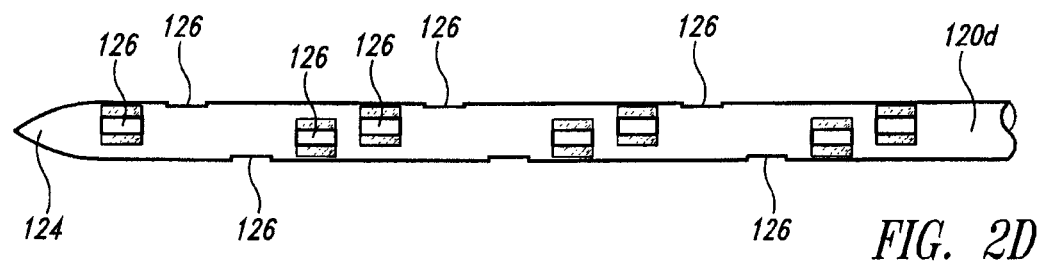

Turning to FIG. 2D, a delivery needle 120d is shown according to another embodiment. Ports 126 of the needle 120d are formed in a spiral pattern, with each port rotated 90° with respect to adjacent ports. In the embodiment shown in FIG. 2D, the ports 126 are formed by wire-electrode electrical discharge machining (wire EDM). In cutting the ports 126, the depth and the length of each cut can be selected to control the port size, while the pitch of the spiral can be selected to control the distribution density. Thus, ports 126 configured as shown in FIG. 2D can be differentially sized or spaced as described with reference to FIGS. 2B and 2C.

In addition to wire EDM, the ports 122, 126 of the needles 120 can be formed by any appropriate method, including, for example, laser cutting, waterjet cutting, chemical etching, mechanical drilling or grinding, etc.

The tip-ends 124 of the needles 120 are shown as being closed and pointed. According to some research, "pencil point" needles, such as, for example, Sprotte and Whitacre needles, may be less damaging to biological tissue than bevel-tipped needles. Additionally, fluids injected into tissue using pencil point side-port needles tend to remain in the tissue rather than leaking from the tissue via a channel formed by the needle. Such considerations are explored in more detail in U.S. Patent Application No. 2004/0191225—see also U.S.

Pat. No. 5,848,996—which are incorporated herein by reference in their entireties. Nevertheless, the scope of the invention is not limited to pencil point needles. Bevel-tipped and blunt-tipped needles can also be employed according to various embodiments. In particular, the inventors have conducted tests using prototypes with blunt-tipped needles, which performed satisfactorily.

Figure 3:
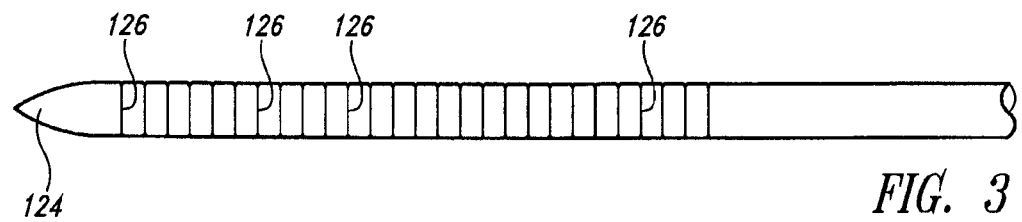

FIG. 3 shows a solid-core delivery needle 130 having a plurality of annular grooves 132. The needle 130 is a "passive delivery" device, meaning that a therapeutic agent is not delivered under pressure from a reservoir but instead is carried into the tissue in the grooves 132. Other passive delivery-type needles include, for example, needles with micro pits over their surfaces, needles coated with nanowire, and needles made from porous materials. Such a needle is immersed in a liquid agent for sufficient time to charge, and is then inserted into the target tissue. In the case of the needle 130 of FIG. 3, the needle can be charged by being briefly dipped into the agent. A porous needle will carry more of the agent, but may require more time to charge, and may likewise need to be left in place in the tissue for a longer period to deliver its charge.

Embodiments are primarily described herein as using active delivery needles, i.e., needles that actively force fluid into the surrounding tissue. However, passive delivery needles such as those described above can also be employed, according to the design parameters of a given application.

Figure 4A:
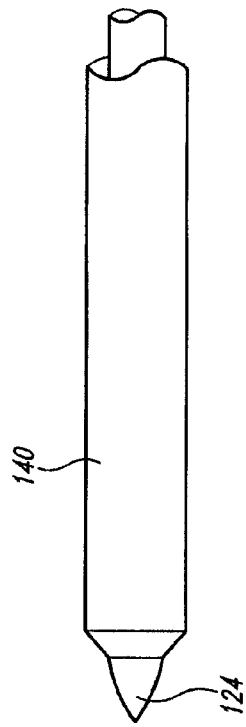
FIGS. 4A and 4B show portions of a delivery needle and an insertion needle in, respectively, an insertion position and a delivery position.
Figure 4B:
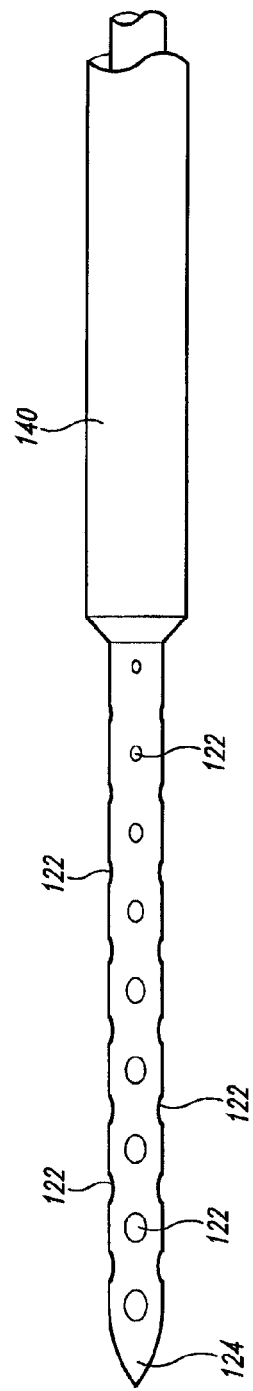

FIGS. 4A and 4B show a portion of an inserter needle 140 and a portion of a delivery needle 120 similar to those described with reference to FIGS. 2A-2D. In FIG. 4A, the inserter needle 140 is positioned such that the tip-end 124 of the delivery needle 120 extends slightly beyond an end of the inserter needle 140. In this configuration, the needle 120 and inserter needle 140 can be inserted through the skin of a subject, such as a patient or test model. The combination of the needle 120 and inserter needle 1406 are configured to have sufficient stiffness to penetrate the skin without bending, and the tapered point of the tip-end 124 assists in the penetration. Additionally, the inserter needle 140 covers the ports 122 of the needle 120 and prevents contamination of the contents of the needle by non-target tissue, and vice-versa. When the tip-end 124 of the needle has penetrated to within a small distance of the target tissue, the inserter needle 140 is held in position while insertion of the needle 120 continues until it is correctly positioned in the target tissue. The insertion distance of the inserter needle 140 can be selected such that the needle 120 is correctly positioned once all of the ports 122 are clear of the inserter needle, as shown in FIG. 2B. In this way, the needle 120 can be provided with maximum protection and support, and the likelihood of contamination can be minimized.

According to an alternate embodiment, a stylette is positioned in the inserter needle to stiffen the needle and prevent collection of a tissue plug during insertion. Once the inserter needle 140 is positioned, the stylette is removed and the delivery needle 120 is inserted.

Figure 5:
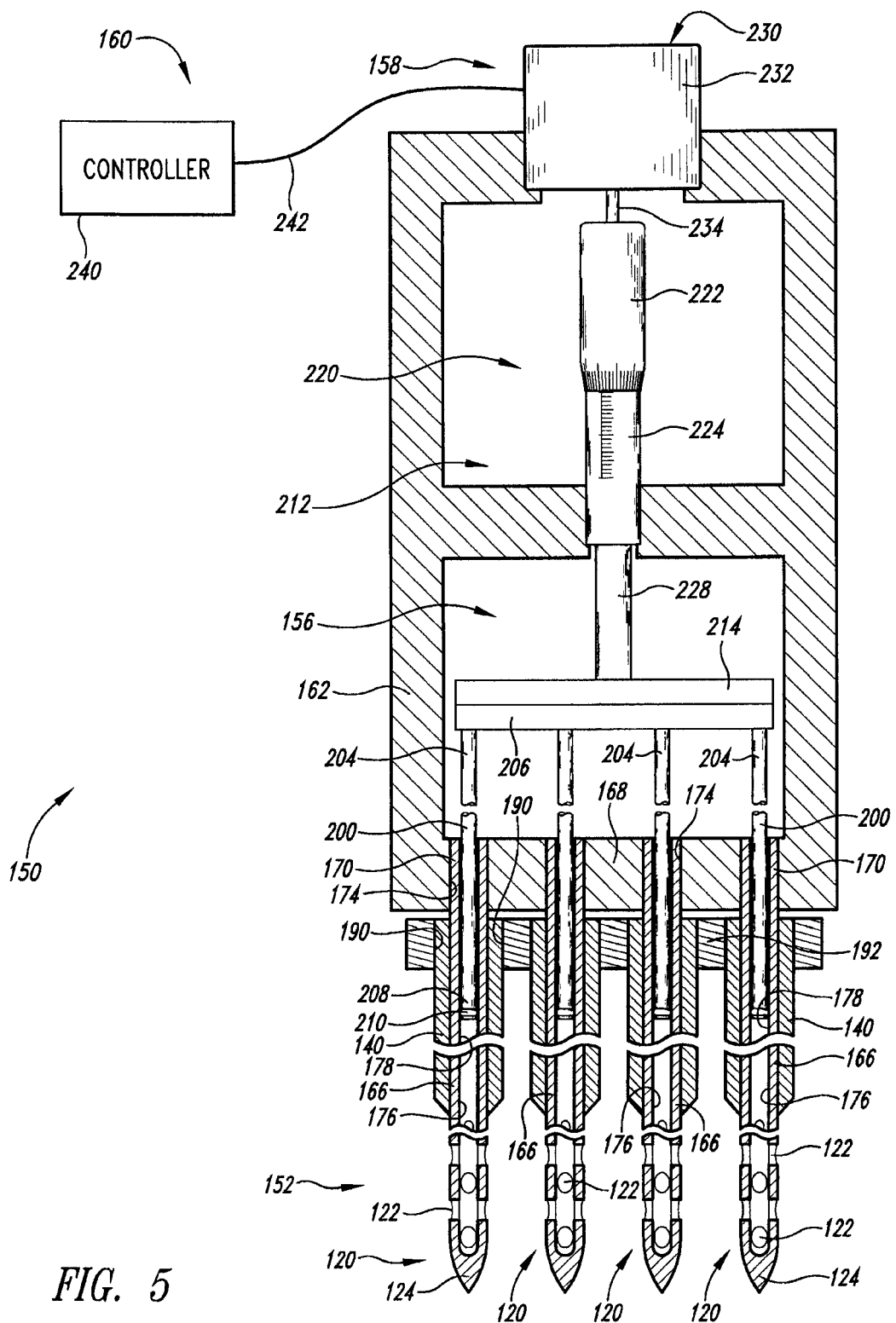
FIG. 5 is a diagrammatic view of a delivery assembly according to an embodiment.

FIG. 5 is a diagrammatic view of a delivery assembly 150 according to another embodiment. The delivery assembly 150 includes a needle array 152, an inserter assembly 154, an actuator assembly 156, a driver assembly 158, a control assembly 160, and a frame 162. The frame 162 provides a substantially rigid structure to which other elements of the assembly 150 are coupled.

The needle array 152 comprises a plurality of needle cylinders 166 and a needle block 168. In the embodiment shown, the needle block 168 is integral with the frame 162. Each of the plurality of needle cylinders 166 is coupled, at a first end 170, in a respective needle aperture 174 extending in the needle block 168, and comprises a lumen 176, having, in the illustrated embodiment, a nominal diameter of 0.15 mm, extending substantially the entire length of the needle cylinder 166. Each needle cylinder 166 includes a reservoir 178 in a region toward the first end 170, a needle 120 in a region toward a second end 180, and a tip-end 124 at the second end 180 of the needle cylinder 166. In the embodiment shown, the tip-end 124 is tapered to a point.

Each delivery needle 120 is defined by a plurality of ports 122 distributed along its length. The length of each of the plurality of needle cylinders 166 and of the respective needles 120 varies according to the embodiment. In one embodiment, each needle cylinder 166 is longer than 15 cm, while according to other embodiments the needle cylinders are each longer than 10 cm, between 5 cm and 10 cm, and as short as 2 cm, respectively. Likewise, according to various embodiments, each of the plurality of delivery needles 120, defined by the portion of the respective needle cylinder 166 along which the ports 122 are spaced, is longer than 1 cm, longer than 2 cm, longer than 4 cm, and longer than 8 cm.

The inserter assembly 154 comprises a plurality of inserter needles 140 coupled to an inserter block 192 in respective inserter apertures 190 extending therein in a configuration that corresponds to the arrangement of the needle cylinders 166 in the needle block 168, such that each of the plurality of needle cylinders 166 can be positioned within a respective one of the plurality of inserter needles 140 as shown in FIG. 5. The inserter assembly 154 is axially slidable over the needle cylinders 166 between a first position, in which only the tip-ends 124 of each of the needle cylinders 166 extend from respective ones of the plurality of inserter needles 140, to a second position, in which the second ends 180 of each of the needle cylinders 166 extends from the respective inserter needle 140 a distance sufficient to clear all of the ports 122 of the respective delivery needle 120.

According to an embodiment, a spacer is provided, configured to be positioned between the inserter block 192 and the needle block 168, sized such that when the inserter block and the needle block are both engaged with the spacer, the inserter block is maintained in the first position. Removal of the spacer permits movement of the inserter block 192 and the needle block 168 relative to each other, to permit placement of the inserter block into the second position, relative to the needle block.

The actuator assembly 156 comprises a plurality of plungers 200 coupled at respective first ends 204 to a plunger block 206 in a configuration that corresponds to the arrangement of the needle cylinders 166 and the inserter needles 140 such that a second end 208 of each of the plurality of plungers 200 can be positioned within the reservoir 178 of a respective one of the plurality of the needle cylinders 166 as shown. An O-ring 210 is provided at the second end 208 of each of the plurality of plungers 200 to sealingly engage the wall of the respective lumen 176. The actuator assembly 156 also comprises an actuator 212 coupled to an actuator block 214, which in turn is rigidly coupled to the plunger block 206. In the embodiment shown, the actuator 212 comprises a micrometer device 220 having a thimble 222, a barrel 224, and a spindle 228 such as are well known in the art. The barrel 224 is rigidly coupled to the frame 162 while the spindle 228 is rotatably coupled to the actuator block 568 so as to control translational movement of the actuator block relative to the frame 162. The micrometer device 568 is calibrated in 0.01 mm increments, with a spindle travel of 0.5 mm per rotation of the thimble 222 and a maximum stroke of 15 mm. Thus, each complete rotation of the thimble moves each of the plurality of plungers 0.5 mm within the lumen 178 of the respective needle cylinder 166 and displaces about 0.0001 cm³ of volume, or 0.1 nL per revolution. Thus, given a maximum stroke of 15 mm, the maximum dispensing capacity of each of the plurality of needles 120 is about 3 nL.

The driver assembly 158 comprises a stepper motor 230 such as is well known in the art, and that includes a motor casing 232, a motor shaft 234 coupled to a rotor of the motor 230, and other elements such as are well known in the art. The motor casing 232 is rigidly coupled to the frame 162, and the motor shaft 234 is slidably coupled to the thimble 222 of the micrometer device 568 while being rotationally locked therewith, such as via a spline coupling, for example. Accordingly, rotational force from the motor shaft 234 is transmitted to the thimble 222, while axial movement of the thimble is not limited by the motor shaft. Such couplings are well known in the mechanical arts. The stepper motor 230 of the illustrated embodiment is configured to divide each rotation into 125 steps. Thus, each incremental rotational step of the motor 230 rotates the thimble about 3°, displacing a volume of about 0.8 pL per reservoir 178.

The controller assembly 160 includes a controller 240 and a control cable 242 that extends from the controller to the stepper motor 230. Signals for controlling direction, speed, and degree of rotation of the motor shaft 234 are transmitted from the controller 240 to the stepper motor 230 via the control cable 242 in a manner that is well known in the field to which such motors belong. According to an embodiment, the controller is programmable. A user can program the controller to control a speed of delivery of a fluid from the delivery needles 120 by selecting the speed of rotation, and a volume of fluid delivered by selecting the number of partial and complete rotations of the rotor. According to another embodiment, the controller is manually operated, such that a user controls a rate and direction of rotation of the motor 230 in real time. According to a third embodiment, the driver and controller assemblies are omitted, and a user controls fluid delivery by manually rotating the thimble 222 of the actuator assembly 212.

Charging the reservoirs 178 can be accomplished in a number of ways. For example, a charging vessel can be provided that includes a plurality of cups or compartments in an arrangement that corresponds to the arrangement of the needle cylinders 166. The user first places a selected fluidic agent or combination of agents in each of the cups. The delivery assembly 150 of FIG. 5 is positioned with the needle cylinders pointing downward as shown in the drawing, and the spindle 228 of the actuator 212 fully extended. The frame 162 is lowered until the needles 120 are fully immersed in the fluids in the respective cups. The motor 230 is then controlled to rotate in the reverse direction, drawing the spindle 228 inward and pulling the plungers 200 upward. This in turn creates a negative pressure in the reservoirs 178 relative to ambient, drawing the fluids into the needle cylinders 166 via the needle ports 122. When the reservoirs are sufficiently charged, rotation of the rotor is halted and the needle array 152 is withdrawn from the charging vessel.

In order to deliver the charge, according to one embodiment, each of the needle cylinders 166 of the needle array 152 is positioned in a respective one of the inserter needles 140 of the inserter assembly 154 so that the tip-ends 178 of the needles 120 protrude from the inserter needles 140, substantially as described with reference to FIG. 4A. The delivery assembly 150 is then positioned in axial alignment with a target tissue region of a subject and translated axially so that the tip-ends of the needles 120 penetrate the subject's skin. Axial translation of the delivery assembly 150 continues until the tip-ends 124 of the needle cylinders 166 have penetrated to within a selected distance of the target tissue region. The inserter assembly 154 is then held in position while the frame 162 and the elements coupled thereto continue to move axially, such that the needles 120 extend into the target tissue region. When the needles 120 are correctly positioned, movement of the delivery assembly 150 is halted and the frame 162 is held in position relative to the subject. The stepper motor 230 is then controlled to rotate the thimble 222 in the forward direction so as to cause the spindle 228 to extend, driving the plungers 200 into the needle cylinders 166 and creating an overpressure in the respective reservoirs 178, thereby forcing fluid from the reservoirs to the target tissue region via the ports 122 of the delivery needles 120.

Delivery can be performed in a few seconds, or it can be extended over minutes or hours under a relatively low overpressure to promote complete absorption of the fluid into the surrounding tissue. According to the embodiment described with reference to FIG. 5, the stepper motor 230 can be controlled to rotate the rotor fast enough to depress the plungers 200 the full 15 mm in less than one second, or slow enough that a single rotation can take many hours.

Figure 6:
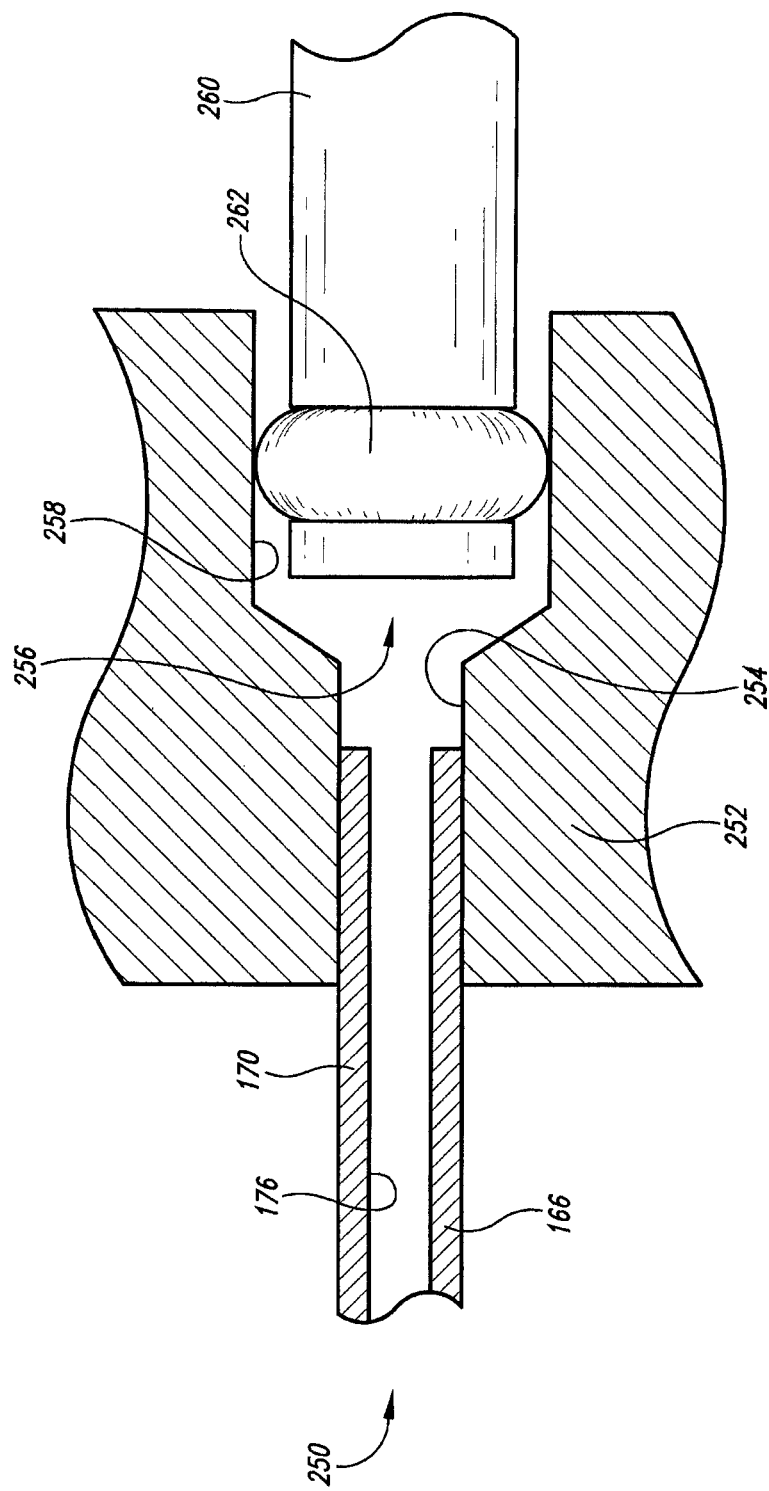
FIG. 6 shows a portion of a needle array, including a reservoir, according to an embodiment.

FIG. 6 shows a portion of a needle array 250 according to another embodiment. A portion of a needle cylinder 166 is shown, together with a portion of a needle block 252. The first end 170 of the needle cylinder 166 is coupled to a first portion 254 of an aperture 256 extending in the needle block 252. The aperture 256 includes the first portion 254, sized to receive the needle cylinder 166, and a second portion 258 having an increased diameter. In the embodiment shown, the diameter of the second portion 258 has a diameter of 0.75 mm. The second portion 258 defines a reservoir that is in fluid communication with the needle cylinder 166. The second end of a plunger 260 is positioned in the second portion 258, with an O-ring 262 sealingly engaged therein.

In the arrangement described with reference to the delivery assembly 150 of FIG. 5, the second end of each of the plurality of plungers 200 is positioned in a respective one of the needle cylinders 166, and the reservoirs 178 are comprised by the needle cylinders. Thus, axial movement of one of the plurality of plungers 200 within the lumen 176 of a respective needle cylinder 166 displaces a volume equal to a transverse cross-sectional area of the lumen, multiplied by the distance of travel of the plunger. In contrast, because of the diameter of the second portion 258 of the aperture 256 of FIG. 6, relative to the diameter of the lumen 176, axial movement of the plunger 260 displaces a volume that is greater than the volume displaced by a plunger 200 of FIG. 5 by a factor of 25, for a given distance of travel. Conversely, to displace an equal volume of the reservoir 178, a plunger 200 of FIG. 5 must travel 25 times as far as the plunger 260 in the second portion 258 of the aperture. Thus, given otherwise identical elements, the delivery assembly 150 of FIG. 5 is capable of accurately metering delivery of smaller quantities of fluid than a similar assembly having reservoirs and plungers configured as described with reference to FIG. 6, while the latter is capable of delivering larger quantities of fluid for a given plunger stroke length; up to 75 nL over a stroke of 15 mm vs. 3 nL for the embodiment of FIG. 5. Of course, the values given are exemplary; one of ordinary skill will recognize that the needle sizes as well as reservoir sizes can be selected to accommodate particular requirements.

Figure 7:
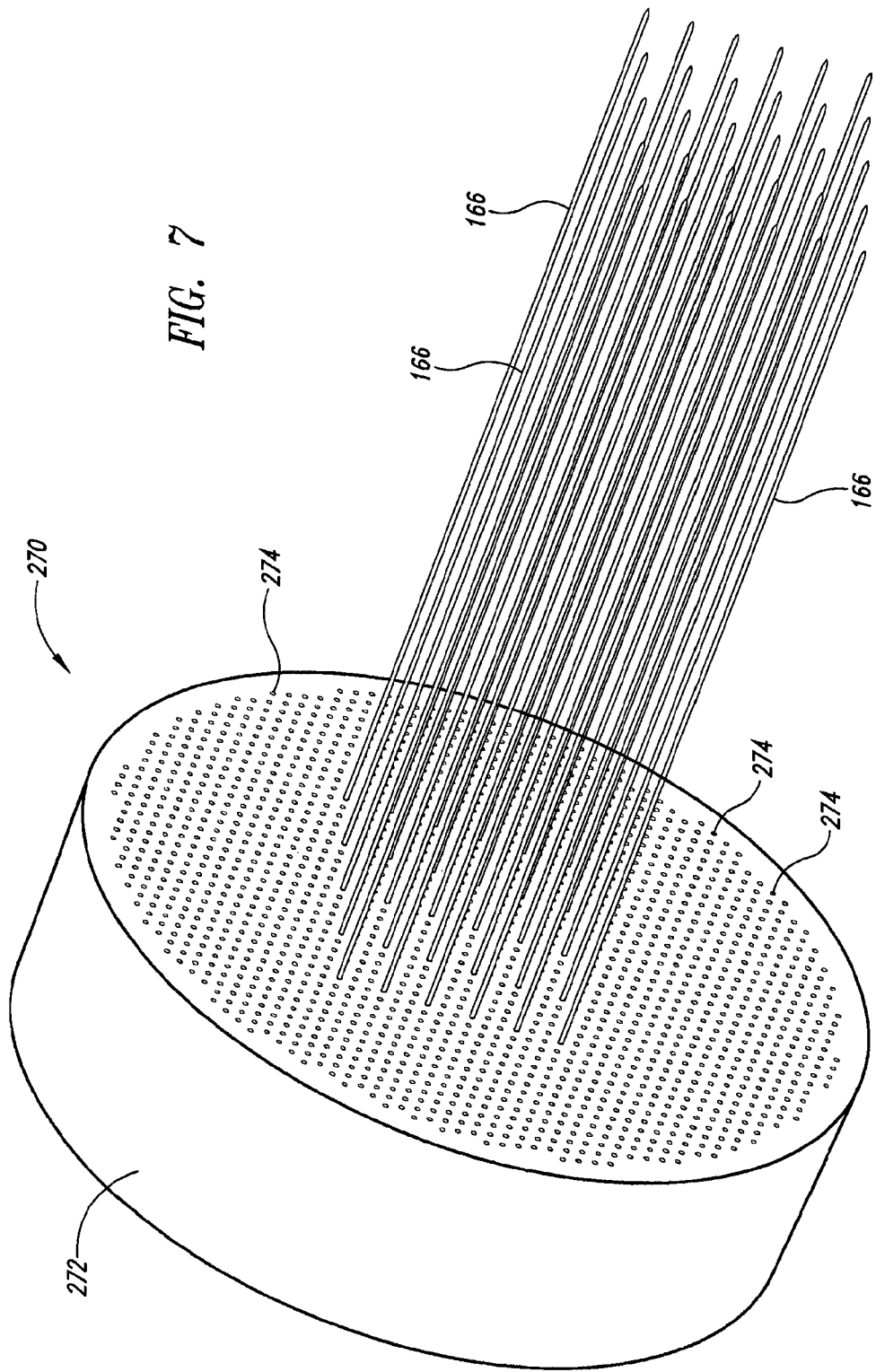
FIG. 7 shows elements of a delivery assembly according to another embodiment.

Turning now to FIG. 7, elements of a delivery assembly 270 are shown according to another embodiment. A needle block 272 includes a large plurality of needle apertures 274 extending therethrough, arranged in a closely spaced array.

Needle cylinders 166 are provided separately, in various assortments of lengths and numbers, sizes, and spacings of ports.

In use, a user selects a number of needles to be used for a particular procedure, and selects the particular needle cylinders 166, placing each in a respective one of the plurality of apertures 274 of the needle block, in an arrangement that is selected for the particular procedure. The user may require only a small number of needles, such as one to five, for example, or may require hundreds or thousands of needles. Furthermore, the needle cylinders 166 can be of varying lengths and configurations. The user selects the arrangement of the needle cylinders 166 in the needle block 272, and their respective lengths and configurations, at least in part according to factors such as the size, shape, and position of a target tissue region in a subject's body, the desired distribution density of fluid in the target tissue region, the permeability of the target tissue, etc.

The needle cylinders 166 can be affixed in the apertures 274 by any appropriate means, including, for example, soldering, brazing, and by adhesive. Alternatively, the needle cylinders 166 can be sized and configured to be fixed in place by an interference fit, such that, for example, the first end of each needle cylinder has a fractionally increased outer diameter. The user drops each needle cylinder into a respective aperture, tip-end first, then pulls the needle cylinder into the aperture from the other side of the needle block until the first end is firmly engaged in the aperture. A plunger block and an inserter block are also provided, with respective pluralities of apertures in arrays corresponding to the array of needle apertures of the needle block. The user loads plungers 200 and inserter needles 140 concurrently with the needle cylinders 166 for operation in a delivery assembly similar to that described with reference to FIG. 5. Provided the method used to attach the needle cylinders 166 in place can be reversed, the needle block 272 can be reused repeatedly for different procedures.

The needle block 272 shown in FIG. 7 is about 5 cm in diameter, 1 cm in thickness, and has approximately 1,600 apertures, spaced about 1 mm apart. According to other embodiments, the needle block can be any appropriate shape and size, from as small as 1 or 2 centimeters across to as large as ten or more centimeters across, and can have any number of apertures, from ten or fewer to several thousand. According to various embodiments, the needle block is provided, for example, with 200, 400, and 800 apertures. The large number of apertures provides significant freedom to a user to control spacing between needles as well as the particular pattern of the array. The needle block 272 is shown with a hexagonal grid array of apertures. The apertures can also be arranged in other grid configurations, such as, for example, rectangular and quincunx. The needle cylinders shown are about 5 cm in length, but this too is merely exemplary.

The delivery actuators of previous embodiments have been described as plungers. However, any suitable actuator can be used to control an amount of therapeutic agent delivered from the reservoirs into the needle. For example, fluid pressure such as by compressed air or pressurized liquid can be used to control an amount of therapeutic agent delivered to a region of biological tissue via the reservoirs and needles.

Figure 8:
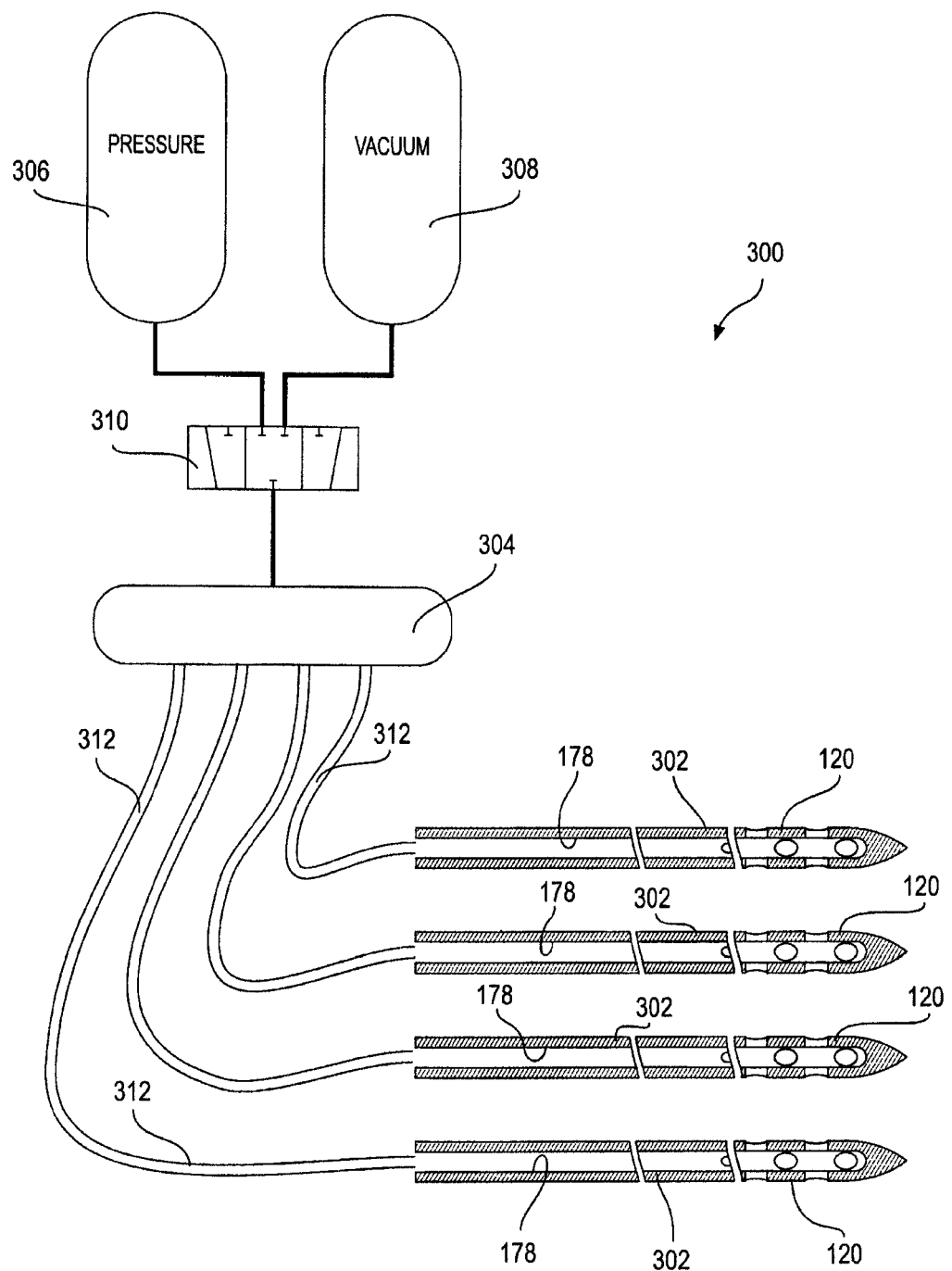
FIG. 8 is a diagrammatic view of a delivery assembly according to a further embodiment.

Referring now to FIG. 8, a delivery assembly 300 is shown, according to another embodiment. The delivery assembly 300 includes a plurality of needle cylinders 302 comprising respective reservoirs 178 and needles 120. Fluid couplings 312 place the needle cylinders 302 in fluid communication with a manifold 304. A fluid pressure source 306 and a fluid vacuum source 308 can each be placed in fluid communication with the manifold 304 by operation of a valve 310.

According to the embodiment of FIG. 8, the needle cylinders 302 are not fixed with respect to each other, but can be individually emplaced, in a target tissue region, for example. The reservoirs are first charged, by placing the delivery needles 120 in a selected fluid, e.g., a therapeutic agent or respective therapeutic agent, and the fluid vacuum source is placed in fluid communication with the manifold, drawing a negative pressure into the reservoirs and drawing the agent into the needles. The user then positions the needles 120 in the target tissue region. When they are all in place, the manifold 304 is pressurized, forcing fluid from the reservoirs of each of the needle cylinders 166 via the ports 122 of the respective delivery needles. While FIG. 8 shows a simple fluid circuit, it will be understood that in practice such a circuit could include any of valves, pressure regulator, peristaltic pump, microfluidic pump, vacuum accumulator, compressor, controller, etc., all of which are well known in the art, and within the abilities of one of ordinary skill to select and configure for a given application.

According to an embodiment, solid tissue into which a plurality of therapeutic agents have been delivered is subsequently resected from the subject and evaluated. For example, in a case where the target tissue is a cancerous tumor, the plurality of agents injected therein can include some agents whose efficacy or effect on such tumors is under investigation. By injecting the various agents in vivo then waiting a selected period before removing the tumor, the effect of the agents on the tumor in situ can be investigated. This preserves the tumor microenvironment and distinguishes this method from current ex vivo or in vitro therapeutics evaluation methods. Assuming that the needles used are configured to deliver a substantially equal amount of fluid at any given location along their length, as described above with reference to FIGS. 2B-2D, the agent delivered by each of the needles is evenly distributed to the surrounding tissue along the delivery axis on which the respective needle 120 was positioned during the delivery of the agent to the tumor 320. Over time, each agent permeates outward from its delivery axis to a greater or lesser degree, depending on factors such as, for example, the density of the surrounding tissue, the viscosity and composition of the agent, the wettability of the tissue by the respective agent, etc. Typically, the portions of the tissue into which the agents spread are approximately column-shaped regions coaxial with the respective delivery axes.

According to various embodiments, a region of tissue is left in place for some period of time before being resected. For example, 48-72 hours following delivery is thought to be generally sufficient for a tumor to exhibit a detectable response. In other cases, the wait period may be hours, days, or weeks. According to some embodiments, the tissue region is imaged using known methods to precisely locate the target region of tissue prior to insertion of the needles. The region may be imaged repeatedly before and after delivery of the plurality of agents to the region of tissue.

According to other embodiments, a plurality of agents are delivered to a portion of tissue via respective ones of a plurality of needles of a needle array after the portion of tissue is resected.

Figure 9:
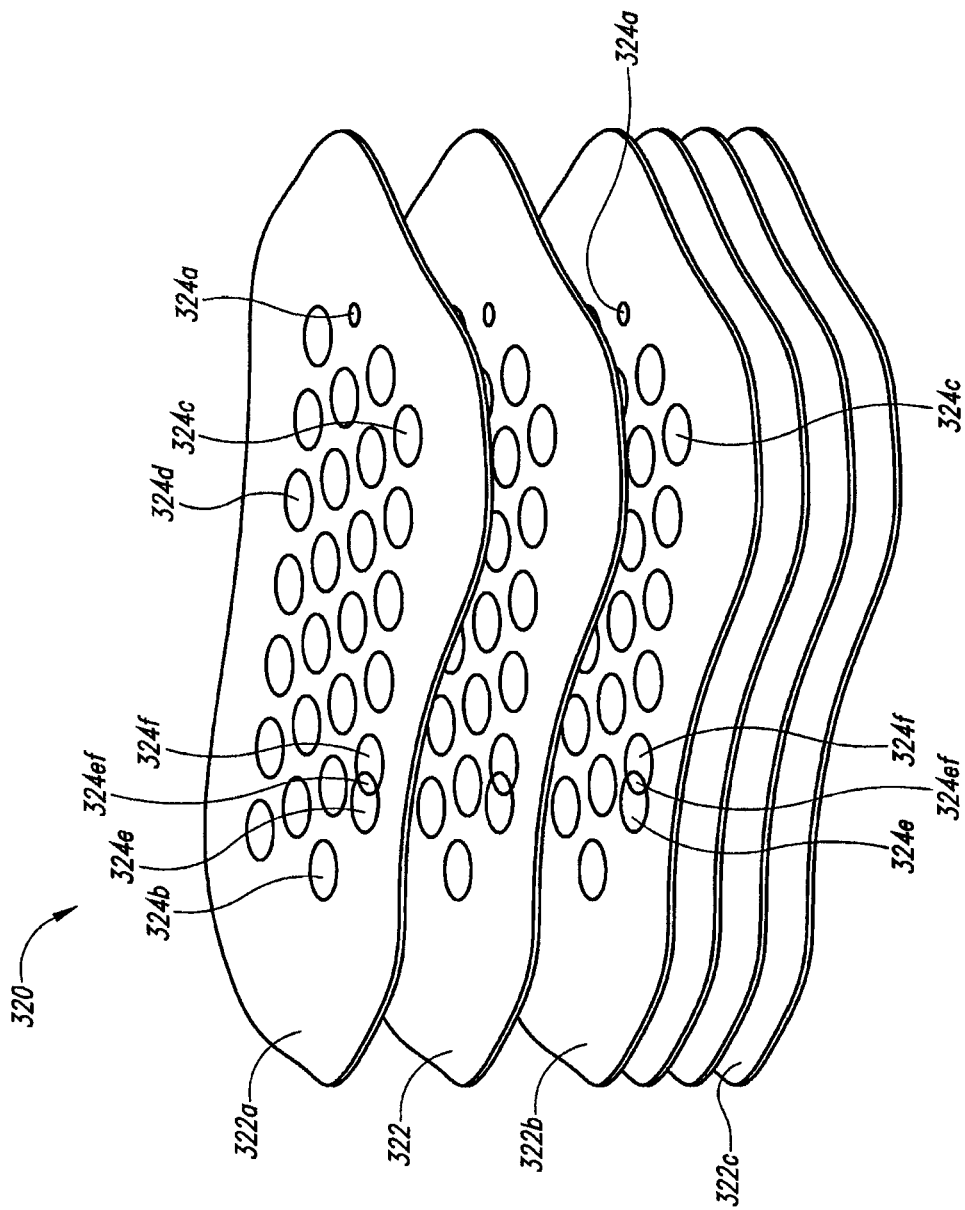
FIG. 9 shows diagrammatically a portion of a tumor illustrating principles of the invention.

Referring now to FIG. 9, a portion of a tumor 320 is shown, following an injection procedure and subsequent resection. The tumor 320 has been sectioned into a plurality of slices 322 along planes that lie substantially normal to the delivery axes. Column-shaped delivery regions 324 define the regions of permeation of the respective agents, and extend perpendicular to the planes of the sections 322.

Many of the regions 324 may not be easily detectable to a user, so generally at least two readily detectable position markers 324a, 324b are among the agents injected, at widely separated locations. The user can then overlay a template on which the locations of each of the delivery axes is marked, aligning the indicated marker positions of the template with the detectable position markers 324a, 324b of a given section 322, thereby locating the remaining delivery regions 324. The position markers 324a, 324b can be any composition that is detectable by a user. Various exemplary position markers are described in detail elsewhere in this disclosure. According to an embodiment, the position markers are selected to resist permeation and diffusion into the surrounding tissue and to remain concentrated in a narrow column, as shown for example at 324a, so as to be detectable for an extended period after the injection procedure, and to provide an accurate guide for positioning the template.

In addition to position markers, control agents may also be among the agents injected. For example, a negative control can comprise a substance used as a vehicle in others of the agents, and a positive control can comprise a compound of most or all of the agents delivered individually at other delivery axes.

Following sectioning of the tumor 320, a user conducts selected assays on delivery regions 324 of various sections 322 of the tumor 320, as described in more detail later. One benefit of the devices and methods disclosed herein is that, in addition to evaluating the efficacy of a given agent on the tumor, the efficacy of agents at various delivery regions 324 can be evaluated and compared. Additionally, the effect of a given agent on various parts of the tumor can be evaluated, both vertically and horizontally. By comparing the effect of an agent in a delivery region 324c at section 322a, for example, with its effect in the same region 324c at sections 322b and 322c, the effect of that agent on different tissue compositions that may occur vertically can be differentiated. Similarly, the same agent can be delivered at several delivery axes in the array, e.g., 324c and 324d, and the relative effects at those locations in a given section 322 can then be compared, providing horizontal differentiation. As is well known in the art, biological tissue is rarely homogeneous over even relatively small distances. A given agent might have substantially no effect on some tissue structures of a tumor, but might, on the other hand, be extremely effective on others. Such differential effects can be detected and evaluated as described above.

Another valuable aspect that can be evaluated is the effect of multiple agents in regions where they interact within the tissue. Delivery regions 324e and 324f are spaced more closely together than the others, resulting in the respective agents interacting in a region 324ef where the respective delivery regions overlap.

As discussed in the background section of this disclosure, clinical trials for cancer related therapeutics are incredibly expensive and time consuming. It is therefore very important to effectively screen for agents that have relatively greater potential as early in the process as possible. Agents subjected to such screening are sometimes referred to as candidate effective agents. One screening method involves placing each candidate agent in a respective Petri dish with a growth medium. A cancerous tumor is reduced to a homogeneous slurry and is distributed among the Petri dishes and incubated. The dishes are later evaluated for indications of cell growth. Agents that appear to have impeded growth of cancer cells may then be advanced for further study.

However, this method is only marginally effective, for several reasons. First, many cancers are known to be nonviable outside a live subject, for reasons such as lack of a blood supply, etc., and fail to grow in vitro under any circumstances. Screening tests like that described are therefore ineffective with these. In some cases it is not known that a particular strain falls in this category prior to conducting the test. The result is that an expensive and time consuming test is inconclusive, and the tumor cannot be salvaged for an alternative test. If the tumor is of a rare strain, it may be some time before another is available for alternative testing.

Second, the reduction process can alter the response characteristics of a tumor. The process involves essentially pureeing the tumor, which completely destroys any structural differentiation, and may render the cancer susceptible to some agents that would have no effect on the same strain in vivo, resulting in a false positive, even though such agents might be useless for treating the cancer in patients. The result is that many such agents are not eliminated until later phases of study, after much more money and effort have been expended.

Third, the same reduction process can also produce false negatives, in which some agents may fail to inhibit cell growth in vitro, but would be effective in treating the same cancer in vivo. This results in the premature elimination of some agents that might otherwise have become effective therapeutic options.

Many false positives or false negatives are generated in the current ex vivo or in vitro art because tumor cells are separated from their microenvironment, e.g., surrounding non-cancerous cells, blood, hormones, paracrine factors, oxygen tension, cell-cell communications, and host immune functions, all of which may influence whether certain therapeutic agents have or do not have activity in cancer cells.

Fourth, even where accurate, only the most general information can be gleaned from such studies because the test conditions do not remotely resemble the conditions in which the cancer normally lives and grows, and in which it is treated therapeutically.

It is also known to inject a test agent into a tumor prior to resection from a subject, for subsequent examination. However, in such tests a single agent is typically injected, so they are not feasible for early screening, but are usually reserved for agents that have already demonstrated significant potential. Even in animal models, it is expensive and time consuming to induce a tumor and allow it to grow to a practical size, which makes extensive early screening by this method impractical.

Finally, even where general efficacy of an agent in treating a particular cancer type, subtype, variant, strain or the like has been demonstrated, it is not uncommon for the cancer of a particular patient to be wholly unresponsive to the agent. The patient is thus exposed to the often extreme discomfort and toxicity of the treatment—not to mention the cost—without significant benefit. Worse, because the agent's ineffectiveness may not be known for a long period while the treatment is ongoing, the opportunity to shift to a different treatment that might have been completely successful may be lost.

Where a similar idiosyncratic response—or lack thereof—occurs in a subject of a drug study, the results of the study can be skewed. To avoid this, it is typically necessary to resort to larger test groups to minimize the statistical impact of non-responding study subjects, which further increases the cost of such studies.

The inventors have recognized that the inability in the known art to accurately position an agent in tissue in vivo, especially with respect to other agents, and the inability to later identify the locations of agents in tissue, prevent more extensive and beneficial use of in vivo injection, and likewise, that if such accuracy could be achieved, significant benefits in research and therapy could be realized.

It has been noted above that the volume of fluid that is delivered by each delivery needle can be vanishingly small, much less than would be a minimal dose required to produce a detectable effect in an adult. Depending on the agent, the effect may nevertheless be detected on the very small region immediately surrounding the delivery site. Accordingly, candidate effective agents can be injected into a tumor, for example, in situ, without danger of harming the subject. Additionally, a significant number of different agents can be simultaneously delivered to respective delivery axes within the tumor.

The procedures described above can be employed to resolve a number of the problems and difficulties that contribute to the cost and delay of developing effective cancer therapies. For example, because the candidate agents are delivered in vivo, the tumor is not otherwise disturbed, and so its reaction to each agent will tend to be indicative of its reaction if exposed to that agent in therapeutically effective quantities. The incidence of false positives and false negatives is significantly reduced.

Second, because relatively large numbers of agents can be delivered to a tumor without significant danger to the subject, it is practical to use the procedure to screen large numbers of candidate agents early in the testing process, perhaps eliminating those that show the least promise, flagging the most promising agents for additional study, or prioritizing candidates for further study.

Third, again because of the large number of agents that can be delivered to a tumor, potential study subjects can be screened for response to particular agents, reducing or eliminating the number of subjects with idiosyncratic responses.

Fourth, when employed in a therapeutic setting, a patient can be tested for response to a large number of treatments and the most promising can be identified early in the process, thereby reducing the number of patients who undergo ineffective treatments and improving the likelihood that a patient will receive the most effective available treatment.

According to an embodiment, a plurality of candidate effective agents are delivered, in vivo, along mutually parallel axes to a region of solid tissue, substantially as described above. The region of solid tissue is subsequently resected from a subject and an effect of each of the plurality of agents on the solid tissue is evaluated. Based on the evaluation, one or more of the plurality of agents are prioritized for further investigation.

According to alternate embodiments, one or more of the plurality of agents are selected or deselected for further investigation, based on the evaluation.

According to another embodiment a plurality of agents that have been shown to have therapeutic benefits are delivered, in vivo, along mutually parallel axes to a region of solid tissue. The region of solid tissue is subsequently resected from a subject and an effect of each of the plurality of agents on the solid tissue is evaluated. Based on the evaluation, one or more of the plurality of agents are prioritized for therapeutic treatment of the subject. According to alternate embodiments, one or more of the plurality of agents are selected or deselected for therapeutic treatment of the subject, based on the evaluation.

According to another embodiment a plurality of agents that are currently under investigation for therapeutic efficacy are delivered, in vivo, along mutually parallel axes to a region of solid tissue in each of a plurality of subjects. The respective regions of solid tissue are subsequently resected from each of the subjects and an effect of each of the plurality of agents on the respective regions of solid tissue is evaluated. Based on the evaluation, one or more of the plurality of subjects are selected as candidates for further study of the therapeutic efficacy of one or more of the agents. According to alternate embodiments, one or more of the plurality of subjects are deselected as candidates for further study of the therapeutic efficacy of one or more of the agents.

According to some embodiments, needle arrays are employed to effectively and broadly deliver therapeutic agents to live and viable tissue (e.g., solid tissue) in a subject, wherein imaging is not required and the tissue is not subsequently resected. The subject may be monitored according to appropriate clinical criteria for assessing clinical improvement. In these and related embodiments, it will be appreciated that significantly higher levels of the therapeutic agent will be achieved within the solid tissue than would be the case if the agent were delivered systemically, although detectable amounts of the therapeutic agent may be subsequently identified outside the solid tissue (e.g., in the circulation). As a non-limiting example, one such embodiment contemplates direct intramuscular introduction of a gene therapy agent for treating muscular dystrophy (e.g., an engineered therapeutic virus, a therapeutic agent-carrying nanoparticle, etc.) to one or more skeletal muscle injection sites in a subject, without the need for imaging, surgery, or histology on biopsy specimens. Of course, periodic monitoring of the circulation for leaked therapeutic agent and/or subsequent analysis of a biopsy specimen, e.g., to assess the effects of the agent on the target tissue, may also be considered.

In other embodiments it is contemplated that the target region in a solid tissue may be imaged using known techniques to evaluate the effects of the agents. The imaging can be by any suitable process or method, including, for example, radiographic imaging, magnetic resonance imaging, positron emission tomogoraphy, biophotonic imaging, etc. In some embodiments, the target region may be imaged repeatedly before, during, and after the delivery process.

Figure 10:
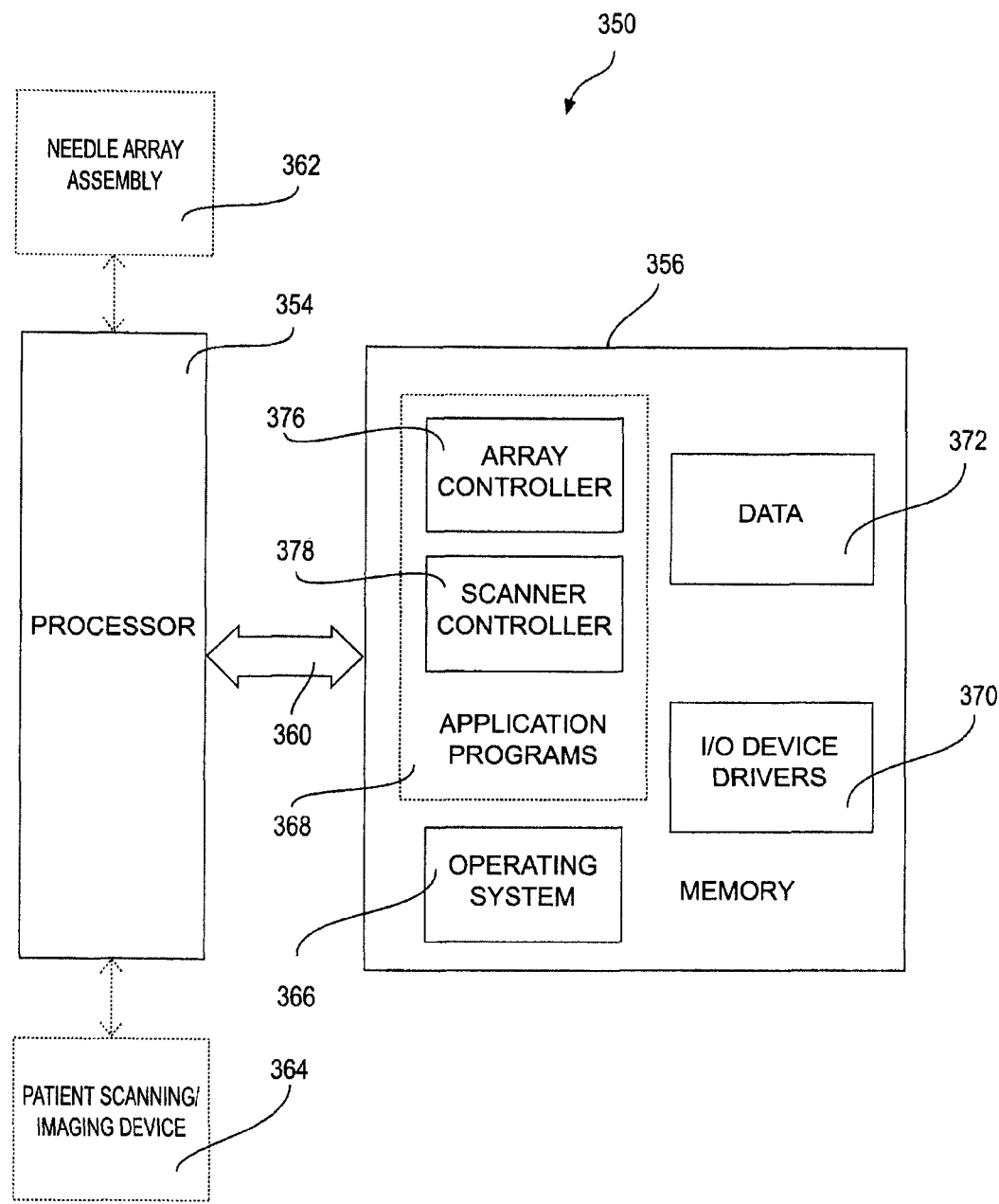
FIG. 10 is a diagram of a data processing system according to an embodiment.

According to the embodiment of FIG. 10, a data processing system 350 is used to carry out or direct operations, and includes a processor 354 and a memory 356. The processor 354 communicates with the memory 356 via an address/data bus 360 and also communicates with a needle array assembly 362 and a patient scanning device 364. The patient scanning device 364 is used, according to an embodiment, to assist in placing the needles of the needle array assembly 362 in a patient in vivo and for non-invasive analysis of target tissue regions using imaging techniques, such as radiographic imaging or nuclear medical assays. The processor 354 can be a commercially available or custom microprocessor, microcontroller, signal processor or the like. The memory 356 can include any memory devices and/or storage media containing the software and data used to implement the functionality circuits and modules.

The memory 356 can any of include several categories of software and data used in the data processing system, such as, for example, an operating system 366, application programs 368; input/output device drivers 370; and data 372. The application programs 368 are illustrative of the programs that implement the various features of the circuits and modules according to some embodiments, and the data 372 represents the static and dynamic data used by the application programs 368, the operating system 366, the input/output device drivers 370 and other software programs that may reside in the memory 356.

According to various embodiments, the data processing system 350 may include several modules, including an array controller 376, a scanner controller 378 and the like. The modules may be configured as a single module or additional modules otherwise configured to implement the operations described herein. For example, the array controller 376 can be configured to control the needle array assembly 100 of FIG. 1, by controlling the actuators 116, and consequently, the release of therapeutic agents from the reservoirs 114 via the needles 112. The scanner controller 378 can be configured to control the patient scanning device 364.

Certain embodiments described herein relate to introducing an agent into a solid tissue in a subject, and/or excising all or a portion of a solid tissue from a subject, and/or obtaining one or more biological samples from a solid tissue that may be in a subject, and/or screening one or more subjects for clinical trial eligibility, and/or any number of other methods that may involve a subject, which includes a subject or biological source.

The subject or biological source may be a human or non-human animal, a transgenic or cloned or tissue-engineered (including through the use of stem cells) organism, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments of the invention, the subject or biological source may be suspected of having or being at risk for having a malignant condition, and in certain preferred embodiments of the invention the subject or biological source may be known to be free of a risk or presence of such disease.

Certain preferred embodiments contemplate a subject or biological source that is a human subject such as a patient that has been diagnosed as having or being at risk for developing or acquiring cancer according to art-accepted clinical diagnostic criteria, such as those of the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, New York); Pizzo and Poplack, *Principles and Practice of Pediatric Oncology* (Fourth edition, 2001, Lippincott, Williams and Wilkins, Philadelphia/Ovid, New York); and Vogelstein and Kinzler, *The Genetic Basis of Human Cancer* (Second edition, 2002, McGraw Hill Professional, New York); certain embodiments contemplate a human subject that is known to be free of a risk for having, developing or acquiring cancer by such criteria.

Certain other embodiments contemplate a non-human subject or biological source, for example a non-human primate such as a macaque, chimpanzee, gorilla, vervet, orangutan, baboon or other non-human primate, including such non-human subjects that may be known to the art as preclinical models, including preclinical models for solid tumors and/or other cancers. Certain other embodiments contemplate a non-human subject that is a mammal, for example, a mouse, rat, rabbit, pig, sheep, horse, bovine, goat, gerbil, hamster, guinea pig or other mammal; many such mammals may be subjects that are known to the art as preclinical models for certain diseases or disorders, including solid tumors and/or other cancers (e.g., Talmadge et al., 2007 *Am. J. Pathol.* 170:793; Kerbel, 2003 *Canc. Biol. Therap.* 2(4 Suppl 1):S134; Man et al., 2007 *Canc. Met. Rev.* 26:737; Cespedes et al., 2006 *Clin. Transl. Oncol.* 8:318). The range of embodiments is not intended to be so limited, however, such that there are also contemplated other embodiments in which the subject or biological source may be a non-mammalian vertebrate, for example, another higher vertebrate, or an avian, amphibian or reptilian species, or another subject or biological source.

Biological samples may be provided by obtaining a blood sample, biopsy specimen, tissue explant, organ culture, biological fluid or any other tissue or cell preparation from a subject or a biological source. In certain preferred embodiments the biological sample may be obtained from a solid tissue (e.g., a solid tumor) using the herein described device, for example, by introducing a multiple needle device into a solid tissue, thereby placing a plurality of needles at a plurality of positions in the tissue, and generating negative pressure at one or a plurality of ports of each needle of the multiple needle device under conditions and for a time sufficient to draw into the needles a plurality of biological samples from the plurality of positions in the tissue.

Devices and methods disclosed here may find uses according to certain preferred embodiments for the introduction of agents to, and/or the withdrawal of biological samples from, a solid tissue, which may be present in a subject in vivo including a solid tissue that may be accessed further to a surgical procedure, or that may be excised, for instance incident to a surgical procedure according to standard medical practices.

Solid tissues are well known to the medical arts and may include any cohesive, spatially discrete non-fluid defined anatomic compartment that is substantially the product of multicellular, intercellular, tissue and/or organ architecture, such as a three-dimensionally defined compartment that may comprise or derive its structural integrity from associated connective tissue and may be separated from other body areas by a thin membrane (e.g., meningeal membrane, pericardial membrane, pleural membrane, mucosal membrane, basement membrane, omentum, organ-encapsulating membrane, or the like). Non-limiting exemplary solid tissues may include brain, liver, lung, kidney, prostate, ovary, spleen, lymph node (including tonsil), thyroid, pancreas, heart, skeletal muscle, intestine, larynx, esophagus and stomach. Anatomical locations, morphological properties, histological characterization, and invasive and/or non-invasive access to these and other solid tissues are all well known to those familiar with the relevant arts.

Certain particularly preferred embodiments as disclosed herein relate to a method for selective delivery of a fluid-phase agent to a solid tissue. As also noted above, such selective delivery obviates the need for excessive systemic concentrations of therapeutic or candidate agents in order to achieve therapeutically effective concentrations in the desired solid tissue, thereby avoiding clinically detrimental toxicities to uninvolved tissues and also avoiding undesirable side-effects. Related embodiments contemplate the testing of currently non-approved candidate agents through such selective delivery to a solid tissue. Without wishing to be bound by theory, according to these embodiments, direct effects of the candidate agent on the solid tissue (e.g., solid tumor) can be evaluated by in vivo administration followed by ex vivo analysis of excised tissue, without threatening the health of the subject, because the dose used for direct administration into the solid tissue is far lower than the minimal dose that would otherwise be administered systemically. (The minimal dose is the smallest amount of the agent that will produce a desired physiologic effect in the subject.) Given the minute volumes and low pressures of the present modes of fluid administration, and full or partial patency of the solid tissue as a physical property that promotes retention of the administered fluid (also determinable by existing methodologies, e.g., by imaging and/or by use of a detectable label as a tracer), the agent that is selectively administered to the solid tissue according to the present disclosure is either undetectable outside the solid tissue, or if detectable outside the solid tissue, the agent is present at less (in a statistically significant manner) than the minimal dose.

Such considerations pertain in related embodiments, wherein detection in a solid tissue of an altered physiologic state subsequent to introducing an agent or a plurality of agents includes detecting a degree of permeation of the agent(s) through the solid tissue, detecting a degree of absorption of the agent(s) in the tissue, detecting a physicochemical effect of the agent(s) on the tissue, and/or detecting a pharmacological effect of the agent(s) on the tissue. Assays, including fluorescence assays, of drug permeation or penetration in solid tissues are known in the art and have been described (e.g., Kerr et al., 1987 *Canc. Chemother. Pharmacol.* 19:1 and references cited therein; Nederman et al., 1981 *In Vitro* 17:290; Durand, 1981 *Canc. Res.* 41:3495; Durand, 1989 *JNCI* 81:146; Tunggal et al., 1999 *Clin. Canc. Res.* 5:1583) and may be configured further according to the present disclosure, for instance, through the detection in histological serial sections of a detectable label that has been co-administered to the solid tissue, prior to excision and sectioning, with an agent of interest.

In such embodiments, permeation or penetration refers to the area of retention of an agent in the solid tissue in the immediate vicinity of the needle from which the agent was introduced exclusive of perfusion (entry into and dispersion via any blood vessel), and may include retention of the agent in extracellular space or extracellular matrix or in association with a cell membrane or intracellularly. Permeation may be distinct from a physicochemical effect, which refers to microscopically detectable mechanical disruption of tissue that results from the needle insertion or fluid injection itself, or from non-biological mechanical or chemical tissue disruption caused by the agent (e.g., damage to cell membranes or disintegration of cell-cell junctions). Pharmacological effects include statistically significant alterations of a cell or tissue physiological state that are detectable as consequences of the molecular mechanism of action of the agent, for example, cytoskeletal reorganization, extension or withdrawal of cellular processes, or evidence of biological signal transduction as may be detected using any of a number of known cytological, biochemical, molecular biological or other read-outs. Comparison of serial sections may permit distinguishing the nature of the effect that is detected histologically.

Particularly preferred embodiments include those in which the solid tissue comprises a tumor, wherein agent delivery may be made to, and/or sample retrieval may be made from, the solid tumor. It will be appreciated by persons familiar with the art from the disclosure herein that in the course of practicing certain embodiments described herein, a selected region of a tumor may comprise the site into which the needles of the presently described devices are inserted, introduced or otherwise contacted with the tumor. The region may be selected on any number of bases, including based on imaging that may be conducted before, during or after a step of needle insertion, introduction or contacting, or based on imaging conducted before, during or after excising the solid tissue from a subject, or based on other criteria including but not limited to anatomic location, accessibility in the course of a surgical procedure, degree of vascularization or other criteria.

Solid tumors of any type are contemplated as being suitable for intervention using the devices described herein. In certain preferred embodiments, the solid tumor may be a benign tumor or a malignant tumor, which may further be a primary tumor, an invasive tumor or a metastatic tumor. Certain embodiments contemplate a solid tumor that comprise one of a prostate cancer cell, a breast cancer cell, a colon cancer cell, a lung cancer cell, a brain cancer cell and an ovarian cancer cell, but the invention is not intended to be so limited and other solid tumor types and cancer cell types may be used. For example, the tumor may comprise a cancer selected from adenoma, adenocarcinoma, squamous cell carcinoma, basal cell carcinoma, small cell carcinoma, large cell undifferentiated carcinoma, chondrosarcoma and fibrosarcoma, or the like. As also noted elsewhere herein, art-accepted clinical diagnostic criteria have been established for these and other cancer types, such as those promulgated by the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, New York); Pizzo and Popiack, *Principles and Practice of Pediatric Oncology* (Fourth edition, 2001, Lippincott, Williams and Wilkins, Philadelphia/Ovid, New York); and Vogelstein and Kinzler, *The Genetic Basis of Human Cancer* (Second edition, 2002, McGraw Hill Professional, New York). Other non-limiting examples of typing and characterization of particular cancers are described, e.g., in Ignatiadis et al. (2008 *Pathobiol.* 75:104); Kunz (2008 *Curr. Drug Discov. Technol.* 5:9); and Auman et al. (2008 *Drug Metab. Rev.* 40:303).

An "altered physiologic state" may be any detectable parameter that directly relates to a condition, process, pathway, dynamic structure, state or other activity in a solid tissue (and in preferred embodiments in a solid tumor) including in a region thereof or a portion therefrom, further including a biological sample obtained therefrom, and that permits detection of an altered (e.g., measurably changed in a statistically significant manner relative to an appropriate control) structure or function in a biological sample from a subject or biological source. The methods of the present invention thus pertain in part to such correlation where an indicator of altered physiologic state may be, for example, a cellular or biochemical activity, including as further non-limiting examples, cell viability, cell proliferation, apoptosis, cellular resistance to anti-growth signals, cell motility, cellular expression or elaboration of connective tissue-degrading enzymes, cellular recruitment of angiogenesis, or other criteria as provided herein.

"Altered physiologic state" may refer to any condition or function where any structure or activity that is directly or indirectly related to a solid tissue function has been changed in a statistically significant manner relative to a control or standard, and may have its origin in direct or indirect interactions between a solid tissue constituent and an introduced agent, or in structural or functional changes that occur as the result of interactions between intermediates that may be formed as the result of such interactions, including metabolites, catabolites, substrates, precursors, cofactors and the like.

Additionally, altered physiologic state may include altered signal transduction, respiratory, metabolic, genetic, biosynthetic or other biochemical or biophysical activity in some or all cells or tissues of a subject or biological source, in preferred embodiments in some or all cells of a solid tissue, and in more preferred embodiments in some or all cells of a tumor such as a solid tumor in a solid tissue. As non-limiting examples, altered biological signal transduction, cell viability, cell proliferation, apoptosis, cellular resistance to anti-growth signals, cell motility, cellular expression or elaboration of connective tissue-degrading enzymes, cellular recruitment of angiogenesis, or other criteria including induction of apoptotic pathways and formation of atypical chemical and biochemical crosslinked species within a cell, whether by enzymatic or non-enzymatic mechanisms, may all be regarded as indicative of altered physiologic state. Certain of these and other non-limiting examples are described in greater detail herein.

According to certain presently contemplated embodiments, the efficacy of a candidate agent may be identified by detecting an altered physiologic state as provided herein, including by assessing any of a number of biological parameters characteristic of a cancer cell such as those reviewed by Hanahan and Weinberg (2000 *Cell* 100:57) and in the references cited therein. Therein are disclosed methodologies for determining the effect of a candidate agent on one or more traits exhibited by cancer cells, and detectable by any of a variety of techniques known to the art for determining one or more of (i) an ability to evade apoptosis, (ii) acquisition of self-sufficiency in growth signals, (iii) insensitivity to growth-inhibitory signals, (iv) acquisition of tissue invasive and metastatic phenotype, (v) unlimited replicative potential, and (vi) sustained angiogenesis. Persons skilled in the art are familiar with multiple approaches for detecting the presence of these alterations of physiologic state, which can be adapted to a particular excised tumor system. See, e.g., Bonificano et al. (Eds.) *Current Protocols in Cell Biology,* 2007 John Wiley & Sons, NY; Ausubel et al. (Eds.) *Current Protocols in Molecular Biology,* 2007 John Wiley & Sons, NY; Coligan et al. (Eds.), *Current Protocols in Immunology,* 2007 John Wiley & Sons, NY; Robinson et al. (Eds), *Current Protocols in Cytometry,* 2007 John Wiley & Sons, NY. Non-limiting examples of parameters that may be assayed to identify an altered physiologic state include assays of cell viability, cell division, apoptosis, necrosis, cell surface marker expression, cellular activation state, cellular elaboration of extracellular matrix (ECM) components or of ECM-degrading enzymes, morphometric analysis, extension or retraction of cellular processes, cytoskeletal reorganization, altered gene expression, e.g., by in situ hybridization of immunohistochemistry (e.g., Shibata et al., 2002 *J. Anat.* 200:309) intracellular phosphoprotein localization (e.g., Gavet et al., 1998 *J Cell Sci* 111:3333), and the like.

Selection of agents that are known or candidate oncology agents is understood and determinable by one skilled in the relevant arts (see, e.g., Berkow et al., eds., *The Merck Manual,* 16$^{th}$ edition, Merck and Co., Rahway, N.J., 1992; Goodman et al., eds., *Goodman and Gilman's The Pharmacological Basis of Therapeutics,* 10$^{th}$ edition, Pergamon Press, Inc., Elmsford, N.Y., (2001); *DeVita, Hellman, and Rosenberg's Cancer: Principles and Practice of Oncology* (2008, Lippincott, Williams and Wilkins, Philadelphia/Ovid, New York); Pizzo and Poplack, *Principles and Practice of Pediatric Oncology* (Fourth edition, 2001, Lippincott, Williams and Wilkins, Philadelphia/Ovid, New York); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston, (1985); Osolci al., eds., *Remington's Pharmaceutical Sciences,* 18$^{th}$ edition, Mack Publishing Co., Easton, Pa. (1990); Katzung, *Basic and Clinical Pharmacology,* Appleton and Lange, Norwalk, Conn. (1992)). Candidate agents may be selected from resources that disclose listings of investigational therapeutics, for instance, the National Institutes of Health (Bethesda, Md.) which maintains a database of ongoing and planned clinical trials at its "ClinicalTrials.gov" website.

Candidate agents for use in screening methods and in methods of rating candidate agents for development into therapeutic agents such as a therapeutic agent for treating a solid tumor may be provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons.

For example, a plurality of members of a library of test compounds can be introduced as candidate agents to a region of a solid tumor of known tumor type in each one or a plurality of subjects having a tumor of the known tumor type, by distributing each of the candidate agents to a plurality of positions along an axis within the region in each subject, and after a selected period of time (e.g., a range of time, a minimum time period or a specific time period) the region of solid tumor in which the candidate agents have been introduced can be imaged or removed from each subject, and each region compared by detecting an effect (if any) of each agent on the respective position within the region, for instance, by determining whether an altered physiologic state is present as provided herein, relative to positions in the region that are treated with control agents as provided herein, which would either produce no effect (negative control) or a readily detectable effect (positive control).

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694, PCT/US91/04666, which are hereby incorporated by reference in their entireties) or other compositions that may include small molecules as provided herein (see e.g., PCT/US94/08542, EP 0774464, U.S. Pat. No. 5,798,035, U.S. Pat. No. 5,789,172, U.S. Pat. No. 5,751,629, which are hereby incorporated by reference in their entireties). Those having ordinary skill in the art will appreciate that a diverse assortment of such libraries may be prepared according to established procedures, and tested for their influence on an indicator of altered mitochondrial function, according to the present disclosure.

Other candidate agents may be proteins (including therapeutic proteins), peptides, peptidomimetics, polypeptides, and gene therapy agents (e.g., plasmids, viral vectors, artificial chromosomes and the like containing therapeutic genes or polynucleotides encoding therapeutic products, including coding sequences for small interfering RNA (siRNA), ribozymes and antisense RNA) which in certain further embodiments may comprise an operably linked promoter such as a constitutive promoter or a regulatable promoter, such as an inducible promoter (e.g., IPTG-inducible), a tightly regulated promoter (e.g., a promoter that permits little or no detectable transcription in the absence of its cognate inducer or derepressor) or a tissue-specific promoter. Methodologies for preparing, testing and using these and related agents are known in the art. See, e.g., Ausubel (Ed.), *Current Protocols in Molecular Biology* (2007 John Wiley & Sons, NY); Rosenzweig and Nabel (Eds), *Current Protocols in Human Genetics* (esp. Ch. 13 therein, "Delivery Systems for Gene Therapy", 2008 John Wiley & Sons, NY); Abell, *Advances in Amino Acid Mimetics and Peptidomimetics,* 1997 Elsevier, NY.

Other candidate agents may be antibodies, including naturally occurring, immunologically elicited, chimeric, humanized, recombinant, and other engineered antigen-specific immunoglobulins and artificially generated antigen-binding fragments and derivatives thereof, such as single-chain antibodies, minibodies, Fab fragments, bi-specific antibodies and the like. See, e.g., Coligan et al. (Eds.), *Current Protocols in Immunology* (2007 John Wiley & Sons, NY); Harlow and Lane, *Antibodies: A Laboratory Manual* (1988 Cold Spring Harbor Press, Cold Spring Harbor, N.Y.); Harlow and Lane, *Using Antibodies* (1999 Cold Spring Harbor Press, Cold Spring Harbor, N.Y.).

Pharmaceutically acceptable carriers for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and other ancillary agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id. "Pharmaceutically acceptable salt" refers to salts of drug compounds derived from the combination of such compounds and an organic or inorganic acid (acid addition salts) or an organic or inorganic base (base addition salts). The agents, including drugs, contemplated for use herein may be used in either the free base or salt forms, with both forms being considered as being within the scope of the certain present invention embodiments.

The pharmaceutical compositions that contain one or more agents may be in any form which allows for the composition to be administered to a patient. According to certain preferred embodiments the composition will be in liquid form and the route of administration will comprise administration to a solid tissue as described herein. The term parenteral as used herein includes transcutaneous or subcutaneous injections, and intramuscular, intramedullar and intrasternal techniques.

The pharmaceutical composition is formulated so as to allow the active ingredients contained therein to be bioavailable upon administration of the composition to a subject such as a human patient. Compositions that will be administered to a patient may take the form of one or more doses or dosage units, where for example, a pre-measured fluid volume may comprise a single dosage unit, and a container of one or more compositions (e.g., drugs) in liquid form may hold a plurality of dosage units. A dose of a drug includes all or a portion of a therapeutically effective amount of a particular drug that is to be administered in a manner and over a time sufficient to attain or maintain a desired concentration range of the drug, for instance, a desired concentration range of the drug in the immediate vicinity of a delivery needle in a solid tissue, and where the absolute amount of the drug that comprises a dose will vary according to the drug, the subject, the solid tissue and other criteria with which the skilled practitioner will be familiar in view of the state of the medical and pharmaceutical and related arts. In certain embodiments at least two doses of the drug may be administered, and in certain other embodiments 3, 4, 5, 6, 7, 8, 9, 10 or more doses may be administered.

A liquid pharmaceutical composition as used herein, whether in the form of a solution, suspension or other like form, may include one or more of the following adjuvants: sterile diluents such as water for injection, saline solution, preferably physiological saline, Ringer's solution, saline solution (e.g., normal saline, or isotonic, hypotonic or hypertonic sodium chloride), fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile. It may also be desirable to include other components in the preparation, such as delivery vehicles including but not limited to aluminum salts, water-in-oil emulsions, biodegradable oil vehicles, oil-in-water emulsions, biodegradable microcapsules, hydrogels, and liposomes.

While any suitable carrier known to those of ordinary skill in the art may be employed in the pharmaceutical compositions of this invention, the type of carrier will vary depending on the mode of administration and whether a conventional sustained drug release is also desired. For parenteral administration, such as supplemental injection of drug, the carrier preferably comprises water, saline, alcohol, a fat, a wax or a buffer. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable according to certain embodiments that the microsphere be larger than approximately 25 microns, while other embodiments are not so limited and contemplate other dimensions.

Pharmaceutical compositions may also contain diluents such, as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, an agent (e.g., a therapeutic drug or a candidate drug) is formulated as a lyophilizate using appropriate excipient solutions (e.g., sucrose) as diluents.

For convenience, elements of various embodiments have been described as components of a number of discrete assemblies. However, in practice, elements of some of the assemblies may be omitted or grouped with other assemblies. Accordingly, the particular arrangements of embodiments disclosed above do not impose similar organization on other embodiments or the claims.

When used to refer to agents delivered from needles, the term fluid is to be read broadly to read on any substance capable of flowing through such a needle, including liquids, gases, colloids, suspended solids, etc.

The abstract of the present disclosure is provided as a brief outline of some of the principles of the invention according to one embodiment, and is not intended as a complete or definitive description of any embodiment thereof, nor should it be relied upon to define terms used in the specification or claims. The abstract does not limit the scope of the claims.

Elements of the various embodiments described above can be combined, and further modifications can be made, to provide further embodiments without deviating from the spirit and scope of the invention. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification, but should be construed to include all possible embodiments along with the full scope of equivalents to which such claims are entitled. Accordingly, the claims are not limited by the disclosure.

The invention claimed is:

1. A method for delivery of two or more different agents into a tumor, comprising: introducing two or more needles arranged in an array in a device into said tumor, wherein a first needle and a second needle of said two or more needles are configured to deliver different agents into said tumor and wherein at least one of said two or more agents is a chemotherapy agent and wherein a first agent is delivered through said first needle and a second agent is delivered through said second needle wherein each needle of said two or more needles arranged in an array is configured to deliver a separate agent of said different agents into said tumor.

2. The method of claim 1, wherein said two or more needles arranged in an array comprise six or more needles arranged in an array and wherein said different agents comprise six or more agents.

3. The method of claim 1, wherein said two or more needles arranged in an array comprise ten or more needles arranged in an array and wherein said different agents comprise ten or more agents.

4. The method of claim 1, wherein at least one of said two or more needles is configured for passive delivery of said different agents.

5. The method of claim 1, wherein said two or more needles are configured for fluid pressure delivery of said different agents.

6. The method of claim 1, wherein at least one of said two or more needles comprises micropits over its surface.

7. The method of claim 1, wherein at least one of said two or more needles is charged with said different agents by immersion in said different agents.

8. The method of claim 1, wherein at least one of said two or more needles is made from porous material.

9. The method of claim 1, wherein at least one of said two or more needles comprises a plurality of ports.

10. The method of claim 9, wherein said plurality of ports are sized and positioned to deliver a substantially equal amount of said different agents.

11. The method of claim 9, wherein each port of said plurality of ports is evenly distributed along a portion of a length of said two or more needles.

12. The method of claim 9, wherein a size of each of said plurality of ports is inversely related to a distance of said port from a tip-end of said two or more needles.

13. The method of claim 9, wherein a distribution density of said plurality of ports is inversely related to a distance of said port from a tip-end of said two or more needles.

14. The method of claim 9, wherein said plurality of ports are distributed in a spiral pattern along a length of said two or more needles.

15. The method of claim 9, wherein said plurality of ports are arranged in pairs of ports on opposite sides of said needle with said pair rotated 90 degrees with respect to an adjacent pair of ports along a length of said two or more needles.

16. The method of claim 1, wherein an amount of said different agents delivered to said tumor is less than 1 microliter.

17. The method of claim 1, wherein an amount of said different agents delivered to said tumor is less than 5 microliters.

18. The method of claim 1, wherein at least one of said two or more needles is close-ended.

19. The method of claim 1, wherein said device delivers said different agents to a plurality of different positions within said tumor.

20. The method of claim 1, wherein at least one of said different agents is delivered to said tumor in an amount that is less than a systemically delivered minimal dose required to produce a detectable effect in an adult.

21. The method of claim 1, wherein at least one of said different agents is delivered to said tumor in an amount that is undetectable outside said tumor.

22. The method of claim 1, wherein at least one of said different agents are delivered to said tumor in a therapeutically effective amount.

23. The method of claim 1, wherein at least one of said different agents is delivered to said tumor in an amount substantially equivalent to an amount that could be detected inside said tumor if said agent were delivered systemically.

24. The method of claim 1, wherein said device is linked to a data processing system.

25. The method of claim 24, wherein said data processing system is in communicable connection with said needle array.

26. The method of claim 1, wherein said tumor comprises lymph node tissue.

27. The method of claim 1, wherein said tumor is a tissue selected from the group consisting of: brain, liver, lung, kidney, prostate, ovary, spleen, lymph node, thyroid, pancreas, heart, skeletal muscle, intestine, larynx, esophagus, stomach, and any combination thereof.

28. The method of claim 1, wherein said tumor is a cancer selected from the group consisting of: adenoma, adenocarcinoma, squamous cell carcinoma, basal cell carcinoma, small cell carcinoma, large cell undifferentiated carcinoma, chondrosarcoma, fibrosarcoma, and any combination thereof.

29. The method of claim 1, wherein at least one of said different agents comprises a position marker.

30. The method of claim 29, wherein said position marker correlates to an injection site of at least one of said different agents.

31. The method of claim 1, wherein said device delivers said different agents transcutaneously.

32. The method of claim 1, wherein said device delivers said different agents subcutaneously.

33. The method of claim 1, wherein said device delivers said different agents using a delivery technique selected from the group consisting of: intramuscularly, intramedullarly, intrasternally, and any combination thereof.

34. The method of claim 1, wherein said device delivers said two or more agents directly into said tumor.

35. The method of claim 1, wherein said device delivers said two or more agents into a skin tumor.

36. The method of claim 1, wherein said device is configured to deliver said different agents in vivo.

37. The method of claim 1, wherein said device is configured to deliver said different agents in situ.

38. The method of claim 1, wherein said device is configured to deliver said different agents to said tumor wherein said tumor is ex vivo.

39. The method of claim 1, wherein said device comprises one or more reservoirs and one or more actuators.

40. The method of claim 39, wherein said one or more reservoirs are in fluid communication with said two or more needles and wherein said one or more actuators are operatively coupled to said one or more reservoirs and configured to control a fluid pressure within said one or more reservoirs.

41. The method of claim 1, wherein said device comprises one or more plungers having a first end positioned in a reservoir and a plunger driver coupled to a second end of said one or more plungers.

42. The method of claim 41, wherein said plunger driver is configured to depress said one or more plungers at a selectably variable rate.

43. The method of claim 41, wherein said plunger driver is configured to depress said one or more plungers simultaneously.

44. The method of claim 41, wherein said plunger driver comprises a driver shaft coupled to said one or more plungers and having a threaded region, wherein said plunger driver is configured such that rotation of said driver shaft in a first direction depresses said one or more plungers a distance corresponding to a thread pitch of said threaded region and a number of revolutions of said driver shaft.

45. The method of claim 44, wherein said device further comprises a motor having a rotor coupled to said driver shaft, wherein said rotor and said driver shaft are rotationally fixed with respect to each other.

46. The method of claim 45, wherein said motor controls rotation of said rotor at a selectably variable rate.

47. The method of claim 1 for delivery of six or more agents into a tumor, comprising: introducing six or more needles arranged in an array in a device into said tumor, wherein at least six of said six or more needles are configured to deliver six different agents into said tumor.

48. The method of claim 1, wherein a plurality of chemotherapy agents are delivered.

\* \* \* \* \*